(12) United States Patent
Njar et al.

(10) Patent No.: US 7,960,435 B2
(45) Date of Patent: Jun. 14, 2011

(54) ANTI-CANCER AGENTS AND ANDROGEN INHIBITION ACTIVITY COMPOUND

(75) Inventors: Vincent C. O. Njar, Glen Burnie, MD (US); Puranik Purushottamachar, Philadelphia, PA (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/519,233

(22) PCT Filed: Dec. 14, 2007

(86) PCT No.: PCT/US2007/087631
§ 371 (c)(1),
(2), (4) Date: Jun. 15, 2009

(87) PCT Pub. No.: WO2008/076918
PCT Pub. Date: Jun. 26, 2008

(65) Prior Publication Data
US 2010/0113600 A1    May 6, 2010

Related U.S. Application Data

(60) Provisional application No. 60/875,322, filed on Dec. 15, 2006.

(51) Int. Cl.
*A61K 31/18* (2006.01)
(52) U.S. Cl. .................................................... 514/604
(58) Field of Classification Search .................... 514/604
See application file for complete search history.

(56) References Cited

U.S. PATENT DOCUMENTS

2004/0167128 A1* 8/2004 Comess et al. ............. 514/227.8

FOREIGN PATENT DOCUMENTS

| DE | 1155119 | 7/1961 |
| FR | 1329349 | 6/1963 |
| JP | 30-9326 B4 | 12/1955 |

OTHER PUBLICATIONS

Purushottamachar et al., "First pharmacophore-based identification of androgen receptor down-regulating agents: Discovery of potent anti-prostate cancer agents", Bioorganic & Medicinal Chemistry, 2007, pp. 3413-3421, Vo. 15.

Natarajan et al., "Novel Arylsulfoanilide-Oxindole Hybrid as an Anticancer Agent That Inhibits Translation Initiation", Journal of Medicinal Chemistry, Oct. 7, 2004, pp. 4979-4982, vol. 47, No. 21.
Purushottamachar et al., "Potent anti-prostate cancer agents derived from a novel androgen receptor down-regulating agent", Bioorganic & Medicinal Chemistry, 2008, pp. 3519-3529, vol. 16.
Fanta et al., Abstract of "Derivatives of 2-(nitromethyl)quinoxaline", Journal of Heterocyclic Chemistry, 1966, pp. 525-526, 3(4).
Fadda et al., Abstract of "Synthesis of certain sulfonamides and aminopyranoquinoline derivatives from 4-hydroxyquinoline with biological interest", Pharmazie, 1991, pp. 743-744, 46(10).
Fadda et al., Abstract of "Synthesis of certain sulfonamides and aminopyranoquinoline derivatives from 4-hydroxyquinoline with biological interest", Journal of the Indian Chemical Society, 1991, pp. 393-395, 68(7).
Jeney et al., Abstract of "The bacteriostatic action of nitrated benzenesulfonanilides", Zentralblatt fuer Bakteriologie, Parasitenkunde, Infektionskrankheiten und Hygiene, Abteilung 1: Medizinisch-Hygienische Bakteriologie, Virusforschung und Parasitologie, Originale, 1966, pp. 122-125, 199(1).
Nadvornik et al., Abstract of "Ortho effect in dissociation of substituted N-phenylbenzenesulfonamides", Collection of Czechoslovak Chemical Communications, 2001, pp. 1380-1392, 66(9).
Bunce et al., Abstract of "N-(Nitrophenyl)benzamide and benzenesulfonamide derivatives by nucleopilic aromatic substitution", Organic Preparations and Procedures International, 2004, pp. 482-487, 36(5).
Lutskii et al., Abstract of "Dipole moments of ortho- and meta-substituted benzene- and toluenesulfonamides and—sulfonates", Vestnik Khar-kovskofo Politekhnicheskogo Instituta, 1969, No. 41, pp. 3-5.
Sheppard et al., Abstract of "Discovery and Optimization of Anthranilic Acid Sulfonamides as Inhibitors of Methionine Aminopeptidase-2: A Structural Basis for the Reduction of Albumin Binding", Journal of Medicinal Chemistry, 2006, pp. 3832-3849, 49(13).
International Search Report issued Aug. 11, 2008 in Corresponding International Application No. PCT/US07/87631.

* cited by examiner

*Primary Examiner* — Rei-tsang Shiao
(74) *Attorney, Agent, or Firm* — Westerman, Hattori, Daniels & Adrian, LLP

(57) ABSTRACT

A qualitative 3D pharmacophore model (a common feature based model or Catalyst HipHop algorithm) developed from well-known natural product androgen receptor down-regulating agents (ARDAs). The 3D pharmacophore model is used as a template in virtual screening compounds for new ARDAs. ARDA compounds and compounds that strongly inhibit the growth of human prostate LNCaP cells. The compounds may be used in compositions and methods of inhibiting cell proliferation of a cancer and methods of preventing or treating cancer, including prostate cancer.

7 Claims, 16 Drawing Sheets

1. (-) Epicatechin
$EC_{50} = 13\ \mu M$

2. Quercetin
$EC_{50} = 25\ \mu M$

3. Flufenamic acid
$EC_{50} = 100\text{-}200\ \mu M$

4. Curcumin
$EC_{50} = 35\ \mu M$

5. Vitamin E succinate
$EC_{50} = 38\ \mu M$ a.

b.

a b

ANTI-CANCER AGENTS AND ANDROGEN INHIBITION ACTIVITY COMPOUND

CROSS REFERENCE TO RELATED APPLICATIONS

This Application claims benefit to U.S. Provisional Application 60/875,322, filed Dec. 15, 2006, which is hereby incorporated by reference in its entirety.

STATEMENT REGARDING FEDERALLY SPONSORED RESEARCH OR DEVELOPMENT

This invention was made with government support under Grant No. CA117991 awarded by the National Institutes of Health (NIH). The U.S. government has certain rights in this invention.

FIELD OF THE INVENTION

The present invention generally relates to the field of oncology, and particularly to the regulation of growth factors that stimulate the proliferation of cancerous cells and those that may be over-expressed, such as receptors, in cancerous cells.

BACKGROUND OF THE INVENTION

Prostate cancer (PCA) is the most common cancer among males of Western countries[1A] and is a complex heterogeneous disease that acts differently in different men. The real cause of prostate cancer is still unknown. However, androgen and the androgen receptor (AR) are postulated to play crucial roles in the development of prostate cancer.[2A] The current treatment for prostate cancer is a combination of surgery, radiation, and chemotherapy. Androgen deprivation is a therapy currently in use for both primary and advanced PCA.[1] This treatment exerts its effect on target tissue by either blocking androgen [testosterone (T) and dihydrotestosterone (DHT)] synthesis or preventing binding of androgens to the androgen receptor (AR). The consequence of both strategies is interference with androgenic effects responsible for stimulation of prostate cancer cell growth. However, even the highly androgen-dependent cases of PCA that are initially responsive to androgen deprivation therapy eventually develop resistance due to selection or adaptation of androgen-independent clones.[2,3] For these patients, no therapy has been shown to be effective[4] and new therapeutic strategies are urgently needed.

The therapeutic agents used clinically include steroidal antiandrogens, such as cyproterone acetate, and nonsteroidal antiandrogens, such as flutamide and bicalutamide. The steroidal antiandrogens possess partial agonistic activity and overlapping effects with other hormonal systems, leading to many complications including severe cardiovascular problems, gynecomastia, loss of libido, and erectile dysfunction.[3A,4A,5A] The nonsteroidal antiandrogens show fewer side effects and have improved oral bioavailability; therefore, they are favored over the steroidal antiandrogens. However, antiandrogen withdrawal syndrome has been discovered in patients receiving nonsteroidal antiandrogens for several months.[6A,7A] Long-term drug usage probably leads to mutation of the AR, and the nonsteroidal antiandrogens now exhibit agonistic activity to the mutant AR.[8A] In addition, the clinically available antiandrogens are unable to kill prostate cancer cells, and within one to three years of drug administration, the cancer usually progresses into an androgen refractory phenotype, which is not curable. The poor clinical outcome of advanced metastatic PC highlights the urgent need to develop effective novel agents for prevention and treatment of this disease.

Androgen receptor down-regulating agents (ARDAs) have emerged as an attractive target for the development anti prostate cancer drugs.[5,5A,6A,7A,8A] Until recently most of the agents known as ARDAs were natural chemicals.[11-15]

The androgen receptor (AR) is central to growth signaling in prostate cancer cells and it may be that the AR remains functional and active in androgen-independent/refractory prostate cancer through a variety of mechanisms aimed at increasing the growth response to lower levels of a wide variety of compounds.[5-7] In the castrate environment, prostate cancer cells develop a growth advantage by amplifying or mutating the AR, altering AR co-regulatory molecules and developing ligand-independent AR activation pathways.[8] Indeed, the AR is expressed in all histological types and stages of PCA, including hormone refractory tumors.[9]

Various compounds, hereafter referred to as androgen receptor down-regulating agents (ARDAs), are capable of decreasing the expression and/or function of the AR. Until recently, most of the known ARDAs are dietary compounds (natural products) including, (−)-epicatechin (1), quercetin (2), curcumin (4) and vitamin E succinate (5).[11-15] The potential implication of these dietary chemicals (nutraceuticals) on prevention of development and progression of PCA has recently been reviewed by Young et al.[16] Other agents, such as flufenamic acid[17] (3, a nonsteroidal anti-inflammatory agent) and LAQ824[15] (a histone deacetylase inhibitor), have also been shown to decrease AR expression in LNCaP prostate cancer cells. The structures of these compounds are presented in FIG. 1. All five compounds are found to decrease AR protein and mRNA expression. Furthermore, they were shown to decrease AR promoter activities as well. However, studies with these molecules have shown that the mechanism by which they potentiate their effects on the AR is not clear.[11-14, 17] Recent studies by Nelson and colleagues[19] indicate that the anti-prostate cancer activities of *Scutellaria baicalenisis*, a botanical with a long history of medicinal use in China, was attributed to four compounds that function in part through the inhibition of the AR signaling pathway. Interestingly, the four active compounds from this plant share the same flavone scaffold as that of epicatechin and quercetin. In addition, curcumin continues to be used as a lead compound to design and synthesize analogs as potential antiandrogenic agents for the treatment of prostate cancer.[20-23]

Therefore, it would be desirable to provide new drugs that lead to inhibition of the Androgen synthesis and AR down-regulation and/or AR modulation, which may be useful for preventing the development, progression and treatment of various cancers, such as, for example, prostate cancer. Further, it would be desirable to provide a novel and effective strategy for identifying these types of new drugs.

BRIEF SUMMARY OF THE INVENTION

Accordingly, the present invention provides a novel method for identifying novel ARDAs through the use of pharmacophore-based drug discovery. The current invention further contemplates the use of these identified ARDAs (small molecules) in methods of treatment, screening methods, as diagnostic tools, prognostic tools, and as therapeutics for, for example, the treatment of cancer. In some embodiments, the methodologies, techniques and/or treatments are targeting and/or directed against prostate cancer cells. In other exemplary embodiments, the various capabilities of the current invention may be utilized for various cancer types.

In one embodiment of the current invention a novel methodology for the identification of novel biologically active agents or leads with diverse chemical scaffolds through the use of three-dimensional (3D) generation and database searching is provided. This pharmacophore based methodology includes the step of modeling an exemplary 'active site' from an ARDA. After the model is completed, then it may be used for selectively searching databases of chemical compounds for similarity. Compounds with similar or significantly similar 'active site' structures may be identified as potential targets for development into therapeutics, as screening agents, diagnostic and/or prognostic indicators. It is a further embodiment of the current invention that the model may be used for comparison with heretofore unknown chemical compounds. This may allow for the identification of these compounds as potential targets, as outlined above.

In one embodiment of the present invention a therapeutic is provided. The therapeutic may be capable of at least activity, for example, in two areas: (1) Inhibition of Androgen synthesis and (2) Competition for the Androgen Receptor (AR), which is typically over-expressed in cancerous cells. Each of these "active pathways" may provide for the down-regulation of the proliferation/growth of cancerous cells. As stated previously, Androgen is a cell growth regulator, therefore, a therapeutic which controls the Androgen activity cycle, either by taking away the Androgen hormone itself or by taking away the cell surface receptors for Androgen, may regulate cell growth in a cancerous cell. In one exemplary embodiment, the therapeutic includes a hydrophobic group, an aromatic ring group and two hydrogen bond acceptors. It is contemplated that this chemical structure forms the backbone of various therapeutics and that from this backbone various other therapeutics may be provided which may include various other structures, molecules, catalysts, reagents, and other components as may be contemplated by those of ordinary skill in the art.

Exemplary embodiments of the present invention include pharmaceutical compositions and methods of use or pharmaceutical compositions and as anti-cancer agents.

Exemplary embodiments of the present invention include methods for inhibiting androgen activity in a cell or a tumor by the use of the compounds and pharmaceutical compositions of the present invention.

Exemplary embodiments of the present invention include methods for treating a subject that is afflicted with a cancer and/or a cancerous cell or cells. As used herein, "treat" and all its forms and tenses (including, for example, treat, treating, treated, and treatment) refer to both therapeutic treatment and prophylactic or preventative treatment. Those in need of treatment include those already with a pathological condition of the invention (including, for example, cancer) as well as those in which a pathological condition of the invention is to be prevented. A method may include administering a pharmacologically effective amount of a therapeutic of the current invention, as described above and throughout, wherein the therapeutic promotes the inhibition of Androgen synthesis. Another method may include administering a pharmacologically effective amount of a therapeutic of the current invention, wherein the therapeutic competes for the AR site on the surface of a cancer cell. In another method of the current invention, the administration of a pharmacologically effective amount of a therapeutic of the current invention may be provided, wherein the therapeutic promotes the inhibition of Androgen synthesis and competes for the AR site on the surface of a cancer cell. In yet another method of the current invention, the administration of a pharmacologically effective amount of a therapeutic of the current invention may be provided, wherein the therapeutic promotes the decrease in the expression and/or function of the AR.

In an exemplary embodiment of the present invention a method for screening whether a subject is/is not afflicted with a cancer is provided. For example, a method for assaying or diagnosing for the presence of cancer in a patient, comprising administering to said patient a therapeutically effective amount of the pharmaceutically acceptable composition of the present invention. In addition, monitoring the progression of cancer in a patient may be performed by comprising administering to said patient a therapeutically effective amount of the pharmaceutically acceptable composition of the present invention and repeating said administration at a later time.

The method may include obtaining a sample from the subject, wherein the sample may be of various cells/cell types, bodily fluids, and/or tissues/tissue types. In a next step, the sample is contacted with a compound that includes at least a scaffold of a hydrophobic group, an aromatic ring group and two hydrogen bond acceptors. The scaffold of the compound may further include a "marker" that allows identification of the compound when bound with a cancer cell from the sample. The identification of the complex by the screening process may allow for the determination of the presence of cancer in the subject. Thus, it is contemplated in other exemplary embodiments of the present invention that methods for diagnosing a subject with cancer is provided. The use of various "markers" that may be detected using various techniques and methodologies as may be contemplated by those of skill in the art does not depart from the scope and spirit of the current invention and is encompassed by the present invention.

In another embodiment of the present invention methods for diagnosing/prognosing cancer/cancer progression within a subject is provided. These methods are similar to the screening method, as described above and throughout, at first and include the step of obtaining a sample from the subject, wherein the sample may be of various cells/cell types, bodily fluids, and/or tissues/tissue types. In a next step, the sample is contacted with a compound that includes at least a scaffold of a hydrophobic group, an aromatic ring group and two hydrogen bond acceptors. The scaffold of the compound may further include a "marker" that allows identification of the compound when bound with a cancer cell from the sample. The method allows for the detection, by methods of those known by one of ordinary skill in the art, of the presence of the complex within the sample. From this detection a cancer may be diagnosed or the progression of a cancer may be determined. It is understood to one of ordinary skill in the art, and encompassed by the instant disclosure, that a method of diagnosis and/or prognosis comprises minimum steps of obtaining a sample, analyzing the sample, which includes contacting the sample with compounds of the instant invention, measuring, for example, a predetermined thing, object, or event, and comparing that measurement to a standard whereby a determination can be made as to a diagnosis and/or prognosis. A standard can mean, for example, a standard curve or the prior measurement of, for example, a predetermined thing, object, or event in a specified individual or individuals. In certain embodiments, the later is used as a standard for method of prognosis.

It is to be understood that both the foregoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE SEVERAL VIEWS OF THE DRAWINGS

FIG. 6 (b) 2D mapping of training set and retrieved molecules showing androgen receptor down-regulation activity with chemical features of Hypo1.

FIG. 7. Dose-dependent androgen receptor down-regulation activity of NCI-0002815 (determined by Western blot analysis). The experiments with the other five agents gave similar plots FIG. 8. Dose-dependent curve for inhibition of human prostate LNCaP cells by NCI-0002815. The experiments with the other five agents gave plots that were similar.

Scheme 1: Synthesis of sulphonamide compounds (series A) (6-18)

Scheme 2: Synthesis of arylamide derivative (series B) (19)

Scheme 3: Synthesis of aryl imines and amines (series C) (20-23)

DETAILED DESCRIPTION OF THE INVENTION

Definitions

Unless otherwise noted, technical terms are used according to conventional usage. Definitions of common scientific technical terms may be found, for example, in McGraw-Hill Dictionary of Scientific & Technical Terms published by McGraw-Hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein in the specification, "a" or "an" may mean one or more. As used herein in the claim(s), when used in conjunction with the word "comprising," the words "a" or "an" may mean one or more than one. As used herein "another" may mean at least a second or more. Furthermore, unless otherwise required by context, singular terms shall include pluralities and plural terms shall include the singular.

As used herein, the term "marker" refers to a molecule capable of facilitating detection and/or identification, including, but not limited to, radioactive isotopes, fluorescers, chemiluminescers, chromophores, enzymes, enzyme substrates, enzyme cofactors, enzyme inhibitors, dyes, metal ions, metal sols, ligands (e.g., biotin, strepavidin or haptens) and the like. The term "fluorescer" refers to a substance or a portion thereof that is capable of exhibiting fluorescence in the detectable range. Particular examples of labels which may be used as a part of an invention described herein include, but are not limited to, horse radish peroxidase (HRP), fluorescein, FITC, rhodamine, dansyl, umbelliferone, dimethyl acridinium ester (DMAE), green fluorescent protein (GFP), enhanced green fluorescent protein (eGFP), Texas red, luminol, NADPH and alpha-beta-galactosidase.

As used herein, "androgen inhibition activity" means the ability to inhibit the activity of an androgen, which can be achieved by, for example, activities directed towards the androgen, the androgen receptor, or a combination of the androgen and androgen receptor. Such activities include, for example, decreasing androgen synthesis or concentration (e.g., decreasing transcription, translation or decreasing the half-life of a transcript or post-translational product), AR downregulation and/or AR modulation, and preventing the binding of an androgen to an androgen receptor or competing with an androgen and its binding to an androgen receptor. Activities also include anti-cancer activities.

Detailed Description

Reference will now be made in detail to exemplary embodiments of the invention.

Figure 13:
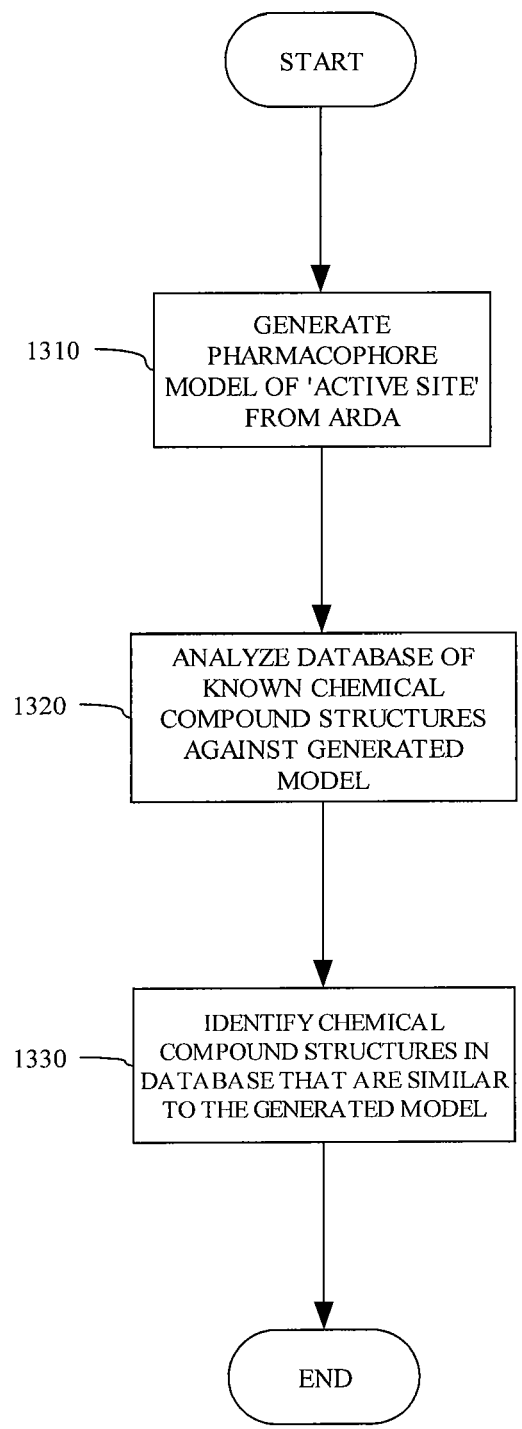
FIG. 13. A block diagram representation of a method for identifying novel chemical compounds with a biologically 'active site' at least significantly similar to the 'active site' of an ARDA.

The current invention provides a method 1300, shown in FIG. 13, for the identification of novel biologically active agents or leads with diverse chemical scaffolds through utilization of three-dimensional (3D) generation and database searching. The increasing number of successful applications of 3D-pharmacophore-based searching in medicinal chemistry clearly demonstrates its utility in the modern drug discovery paradigm.[24-26] Considering the prospects of ARDAs as potential agents for the prevention and treatment of PCA as well as the paucity of potent ARDAs, a first step 1310 of the current invention employed the use of Catalyst HipHop technology to generate a suitable pharmacophore model of the ARDA 'active site' that may be useful for identifying novel ARDAs. A second step 1320 employs the novel pharmacophore model of an ARDA 'active site' for the analysis of multiple (e.g., two) databases of known chemical compound structures.

The analysis performed includes a comparison of the structure of the ADRA 'active site' with that of the compound structures contained within the databases. In a next step 1330, those compounds with similar or at least significant similarity in chemical structure to the model are selectively identified as potential targets for the development of cancer therapeutics, screening agents, diagnostic and/or prognostic markers. The embodiment of the present invention of novel modeling processes led to the discovery of new and potent ARDAs (previously unidentified chemical compounds having at least significantly similar chemical structure to that of the ADRA 'active site'). Lead optimization via rational design and synthesis provided the identification of extremely potent inhibitors of two human prostate cancer cell lines, LNCaP and PC-3. The binding affinities to the mutant and wild-type ARs and effects on LNCaP mutant AR-mediated transcription of two compounds (9 and 11) were able to be determined. It is contemplated that the identified chemical structures may be modified. For instance, they may include various markers, catalysts, excipients, reagents, and the like as contemplated by those of ordinary skill in the art which may promote the effectiveness of the chemical structure when being utilized.

This novel modeling methodology may be employed in comparison analysis with previously unknown chemical compounds and their structures. For example, an unknown chemical compound may be analyzed and its structural features identified. The identification may include a modeling of the structure. From this identification of the structural features of the unknown compound it may be compared against the model of the 'active site' of the ARDA. Where similarity or at least significant similarity is found the compound may be identified as a potential target for further use in the current invention. Similar to both methodologies presented herein, where no similarity or significant similarity is found the compound may be dismissed as not being a potential candidate for further use by the current invention.

Figure 9:
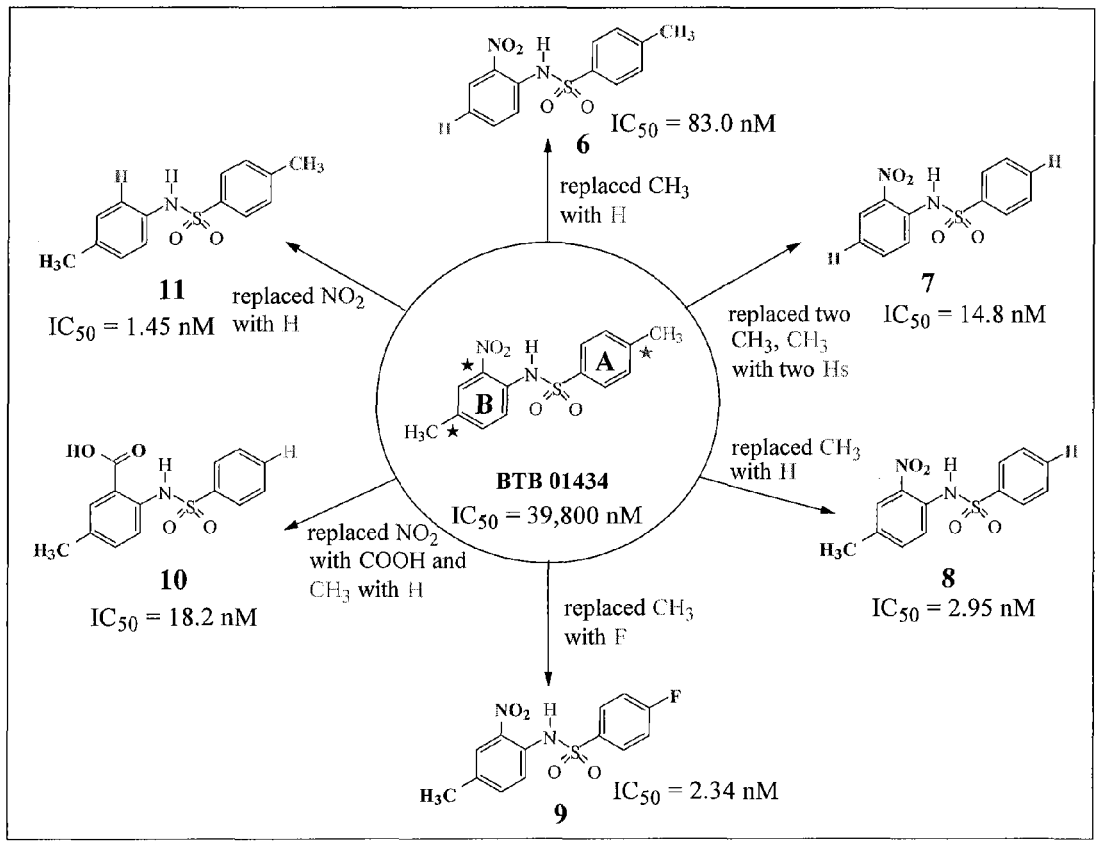
FIG. 9. Structural representation of multiple compounds that may be capable of being developed into therapeutics and/or screening agents for cancer. Lead optimization of BTB01434

In one embodiment, a composition of matter is provided. It is contemplated that the composition of matter may be useful as a therapeutic. A compound of the composition may have various chemical structural features, but contains as a "backbone structure" or "scaffold" a hydrophobic group, one ring aromatic group and two hydrogen bond acceptors. Multiple exemplary embodiments of this scaffold that may be employed in the current invention are compounds 6-11, as shown in FIG. 9. As will be described below, this scaffold is similar or at least significantly similar to the 'active site' of known ARDAs. Therefore, compounds that include this scaffold include a biological activity that is similar or at least significantly similar to known ARDAs activity.

The compound may have formula of structure (1)

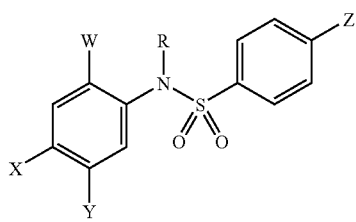

Wherein
W is selected from the group consisting of H, cyano, —NO$_2$, —COOH and a heterocyclic group;

X is selected from H, unsubstituted linear or branched alkyl group and halogen,
Y is selected from H and substituted or unsubstituted linear and branched alkyl group,
Z is selected from H, substituted or unsubstituted linear and branched alkyl group, and
R is selected from H and substituted or unsubstituted linear and branched alkyl group.

The compound may have formula of structure (2)

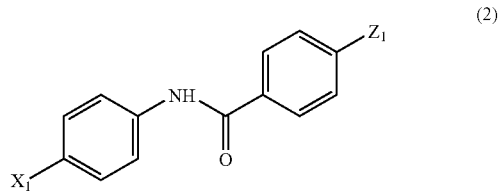

Wherein X$_1$ and Z$_1$ are independently selected from the group consisting of H, unsubstituted linear or branched alkyl group and halogen.

The compound may have formula of structure (3)

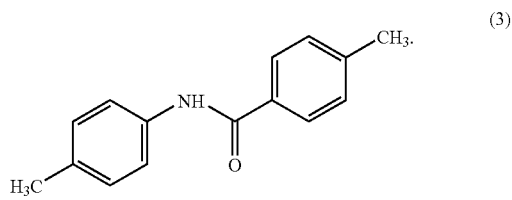

The compound may have formula of structure (4)

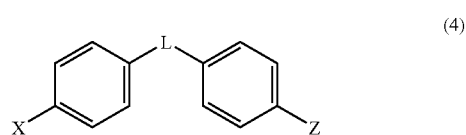

wherein X and Z are independently selected from the group consisting of H and unsubstituted linear or branched alkyl group and L is selected from the group consisting of N=CH, HN—CH$_2$, N=CH, and HN—CH$_2$.

In other embodiments, in the above Formulae (1), (2) and (4), X may be selected from H, methyl and F, Y may be is selected from H, methyl and F, Z may be selected from H and methyl, R may be selected from H and methyl and in W the heterocyclic ring may be a nitrogen containing 5 member heterocyclic group, for example, a 1H-tetrazole.

The compounds that may be produced utilizing the process of the current invention are capable of including various other chemical features as may be contemplated by those of ordinary skill in the art. The various additional chemical components may be included to provide more effective delivery of the compound once placed within a system. The delivery may be enhanced by promoting a more pharmacologically effective amount of the compound reaching a site of action, preferably a cancerous tumor site. The delivery may also be enhanced by promoting a more effective delivery of the compound across a cell membrane or within the cell and across the intra-cellular space.

It is contemplated that the compound may be variously formulated for ingestion to include, for example, a solid form tablet or capsule formulations which may also include various other compounds, such as dextrose and/or phosphate for ease of use and effectiveness. Alternatively, the compound may be formulated as a suspension, emulsion, or sterile solution. Thus, the compound formulation may allow for parenteral (e.g., injection, suppository) and/or topical delivery, such as the direct application to a localized site. A solid oral formulation of the compound may further include a controlled release formulation. This may enhance the functional capabilities by enabling a response over a prolonged period of time.

The current invention provides a method for synthesizing a compound including a structure that is similar or at least significantly similar to the ARDAs 'active site'. In one embodiment shown in Scheme 1, sulfonamide compounds may be synthesized that have a similar or at least significantly similar biological activity as that of the ARDAs 'active site'. It is further shown that the scaffold of some exemplary compounds include the one hydrophobic group, one ring aromatic and two hydrogen bond acceptors. Two exemplary synthesis methodologies of the current invention include (1) refluxing appropriate substituted amines with corresponding aromatic sulfonyl chlorides in pyridine for six hours and (2) solubilizing 2-amino-5-methylbenzoic acid in aqueous $Na_2CO_3$ solution at 60° C. followed by treatment with benzene sulfonyl chloride and then stirring at 80° C. for 6 hours, to produce a carboxylic acid containing compound. The synthesis process may be carried out under various conditions and utilizing various reagents. In one embodiment, the process proceeded under the following conditions and using the following reagents: (1) Pyridine, reflux, 125° C., 6 hours; (2) $Na_2CO_3$, reflux, 80° C., 6 hours.

It is contemplated that the method for synthesizing compounds may further include various functional steps for formulating the compound with an increased delivery capability. For example, a further step may be preparing the compound as a solid form for ingestion. This process may also include the addition of various sugars or other supplements to promote ease of ingestion. In the alternative, the process may include preparing the compound in a form for parenteral delivery, such as in liquid form or as a suspension. Still further formulation processes may be employed without departing from the scope and spirit of the present invention.

Figure 14:
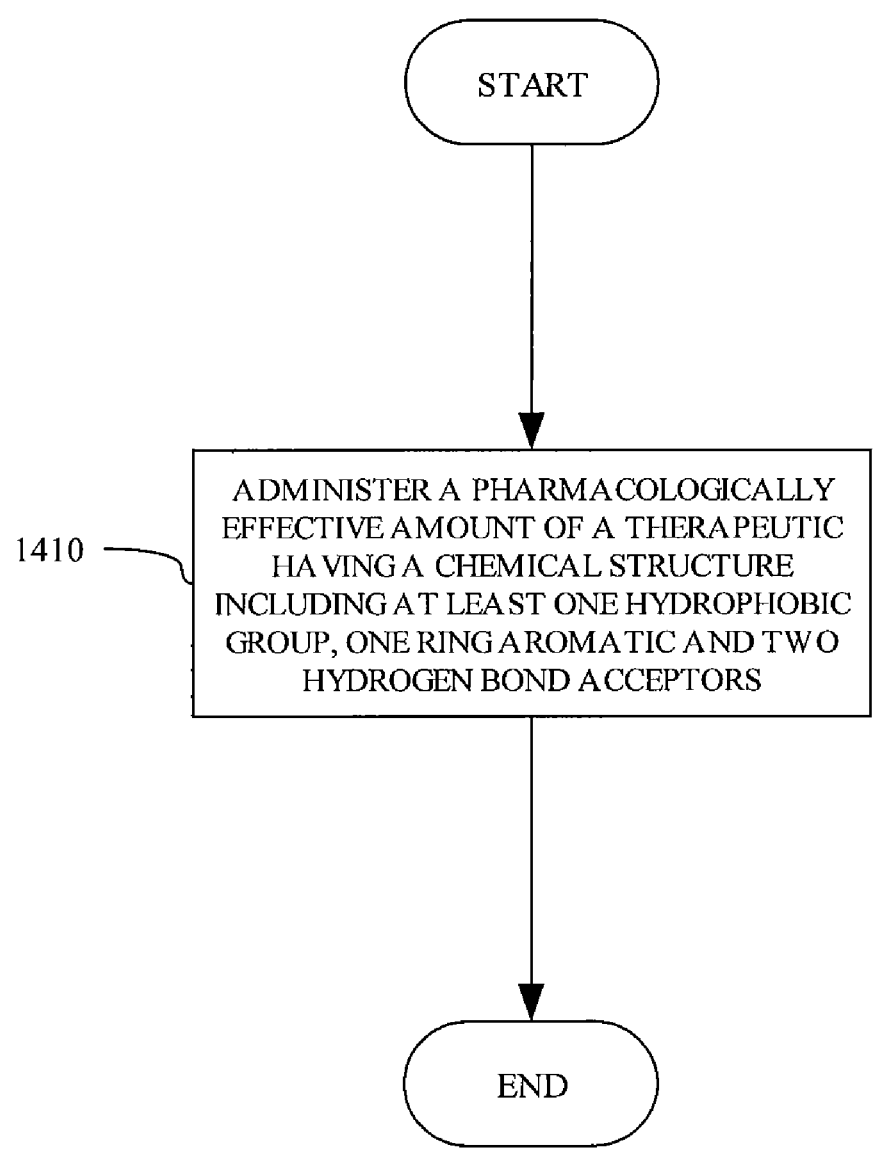
FIG. 14. A block diagram representation of a method of treating a subject having cancer including the use of a therapeutic having a scaffold as previously identified as compounds 6-11, shown in FIG. 9.

A method 1400 of delivering the composition of matter of the current invention to a subject having cancer, is shown in FIG. 14. It is contemplated that the compound(s) of the current invention may be utilized for the treatment of subjects afflicted with cancer. The method includes step 1410 where the subject is administered a pharmacologically effective amount of a composition of matter (therapeutic) at least including one hydrophobic group, one ring aromatic group and two hydrogen bond acceptors. Thus, the therapeutic may have a biological activity similar or at least significantly similar to an ARDAs 'active site' and be able to promote competition for the AR binding site or the prevention of further Androgen synthesis.

It is contemplated that the administration of the therapeutic of method 1400 may occur in various ways utilizing various techniques. For instance, administration may be oral, inhalant, parenteral (by injection or suppository), or otherwise as described above. It is contemplated that the subject may be a mammal and more particularly may be a human male or female.

Figure 15:
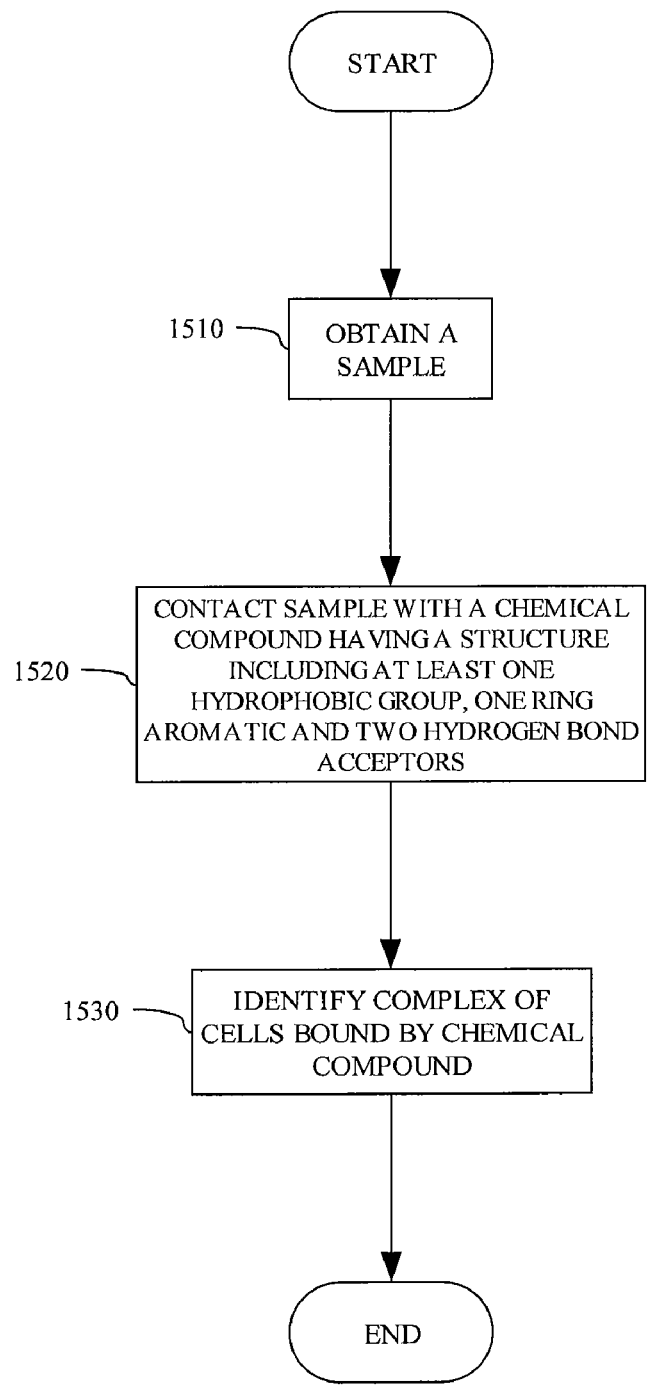
FIG. 15. A block diagram representation of a method of screening a sample obtained from a subject for the presence of cancer.

A method 1500 of screening a sample for the presence of cancer cells is shown in FIG. 15. The method includes the step 1510 of obtaining a sample. Various tissues and/or body fluids obtained from a subject afflicted with cancer may be the source of the sample. In a one embodiment, the cancer is prostate cancer. In another embodiment, the cancer is hormone refractory prostate cancer.

It is contemplated that the various exemplary embodiments of the current invention may address various types of cancer. Non-limiting examples are leukemias, carcinomas, lymphomas, or sarcomas. Examples of such cancers include prostate cancer, lung, esophageal, stomach, cervical, mammary, gliomas, and/or ovarian cancer.

After the sample is obtained, in step 1520, the sample is contacted with a compound that contains at least one hydrophobic group, one ring aromatic group and two hydrogen bond acceptors. Thus, the current method contemplates contacting the sample with a compound that may be similar or at least significantly similar to a therapeutic of the current invention as described above or a compound that has a similar or at least significantly similar biological activity as that of an ARDAs 'active site'. In step 1530 cells of the sample that are bound with the compound from step 1520 are identified. The identification of the bound complex allows for the determination of the presence of cancer within the sample.

It is contemplated that the compound which is placed in contact with the sample includes various markers or indicators that may allow for the identification of the bound complex. These markers may be selected based on the type of assaying technology being employed for identifying the presence of the bound complex. It is further contemplated that the markers may be fluorescent dyes or stains or may include various types of "tags" or "labels", such as radioactive labels.

In additional embodiments, the current invention may allow for the diagnosing and/or prognosing of cancer within a subject. The method may include obtaining a sample from the subject and then contacting the sample with a compound in a manner similar to that described above for the method 1500. Through the identification of the bound complex, such as through identification of a marker, the existence of and/or progression of a cancer may be determined.

Results and Discussion

Figure 1:
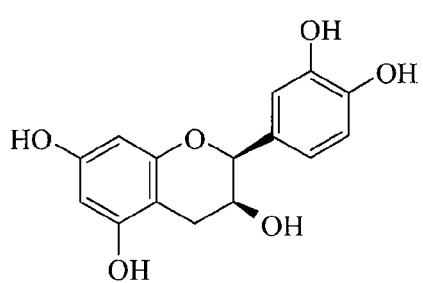
FIG. 1. (Prior Art) Chemical structures of five known androgen receptor down-regulating agents (ARDAs) used to generate the pharmacophore model.
Figure 1:
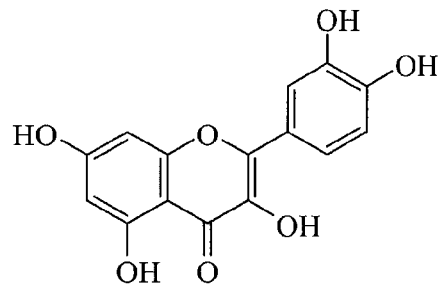
Figure 1:
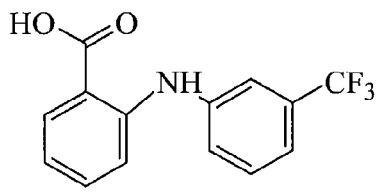
Figure 1:
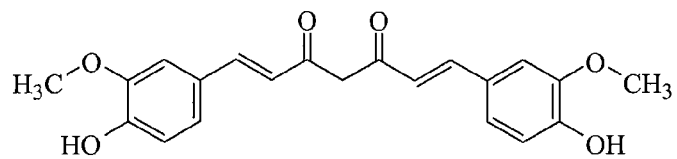
Figure 1:
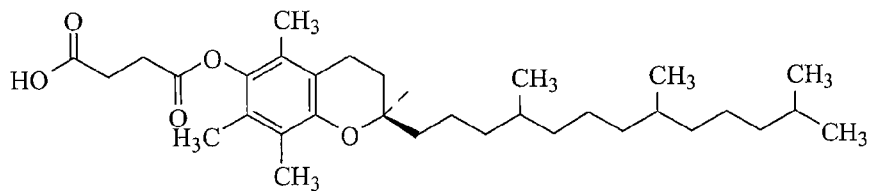
Figure 2:
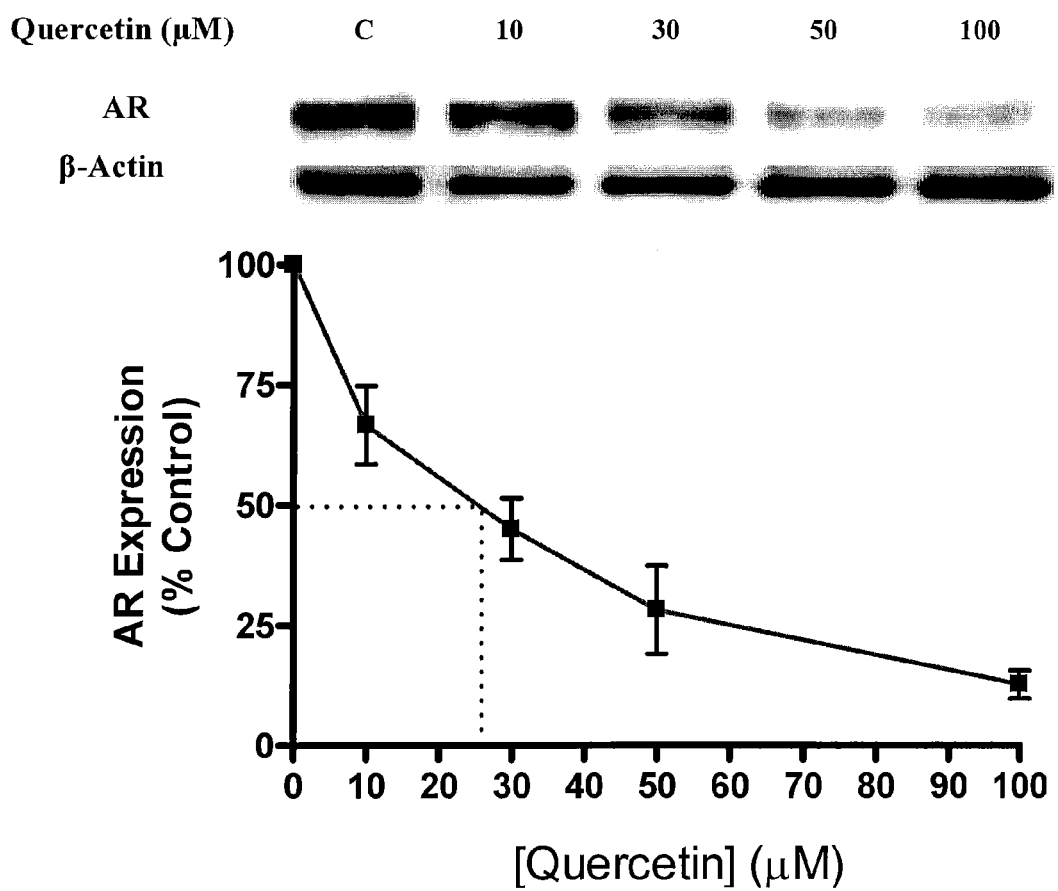
FIG. 2. Dose-dependent androgen receptor down-regulation activity of quercetin (2) (determined by Western blot analysis). The experiments with the other agents (1, 3-5) gave plots that were essentially the same as shown below.

Effects of ARDAs (training set compounds) on AR protein expression: Although the effects of known ARDAs on AR protein levels have been reported by various investigators,[11-18] there are no reports of their Effective Concentration ($EC_{50}$) values. All five known ARDAs (FIG. 1) were evaluated for their ability to decrease AR protein expression in a dose dependent manner and dose response curves were generated to determine their $EC_{50}$ values. Quercetin (2), the most well known naturally occurring AR down-regulating agent in LNCaP cells was found to have an $EC_{50}$ of about 25 µM (FIG. 2). Quercetin, which is a naturally occurring flavanoid, has also been found to decrease the expression of the AR gene at the transcriptional level, thus it was of importance to include this molecule in the training set.[12] The $EC_{50}$ values of all five compounds (13-200 µM range) are presented in Table 1 (below) and show that four out of five compounds, epicatechin (1), quercetin (2), curcumin (4) and vitamin E succinate (5), exhibited low micromolar $EC_{50}$ values. To the best of our knowledge, this appears to be the first report on EC50 values for AR protein expression of these well known ARDAs. The determination of the $EC_{50}$ values for AR protein expression of these well known ARDAs has been heretofore unknown. Although we utilized the LNCaP cell line which contains a mutant AR, it should be noted that most ARDAs have been shown to exhibit similar effects on both the mutant and wild-type ARs.[9,15] It should be stated that these compounds inhibit AR expression at both the transcription and translation levels or at either of these levels. The compounds in the training set possess diverse structures to furnish structural requirements for the three dimensional pharmacophore model generation described hereafter.

TABLE 1

| Compound | $EC_{50}$ values (μM) |
|---|---|
| Epicachetin (1) | 13.0 |
| Quercetin (2) | 25.0 |
| Flufenamic acid (3) | ~200 |
| Curcumin (4) | 35.0 |
| Vitamin E Succinate (5) | 38 |

Common feature-based pharmacophore model: The range of inhibitory activity (~2 log units) and a small set of molecules may decrease the possibility of allowing for the generation of a meaningful activity-based (predictive) pharmacophore model using Catalyst/Hypogen technology. However, on the basis of previous evidence of successful pharmacophore generation for molecules that do not act by the same mechanism of action, but differentially affect a particular molecular target,[30A,31A] the Catalyst/HipHop approach was employed to evaluate the common feature required for binding and the hypothetical geometries adopted by these ligands in their most active forms. Thus, a training set consisting of five ARDAs (1-5, FIG. 1) with AR down-regulation activity through unknown mechanism was utilized for pharmacophore model generation based on common chemical features. A preliminary account of part of this work has been presented.[29A]

A pharmacophore is a representation of generalized molecular features including 3D (hydrophobic groups, charged/ionizable groups, hydrogen bond donor/acceptors), 2D (substructures), and 1D (physical and biological properties) aspects that are considered to be responsible for a desired activity. Two different approaches are applied in automated hypothesis generation. The first is Hypogen, an activity-based alignment derived from a collection of conformational models of compounds spanning activities of 4-5 orders of magnitude (the minimum number of molecules to ensure statistical significance of pharmacophores computed in the Catalyst Hypogen algorithm is 16). The second algorithm in 3D pharmacophore generation within Catalyst is a common feature based alignment of highly potent compounds. The activity of the molecules is not taken into consideration using this model generation mode. HipHop hypotheses are produced by comparing a set of conformational models and a number of 3D configurations of chemical features shared among the training set molecules. Compounds of the training set may or may not fit all features of resulting hypothesis, depending on the settings for the parameters Maximum Omitted Features, Misses, and Complete Misses. The retrieved pharmacophore models are expected to discriminate between active and inactive compounds.[27A] This strategy (HipHop) has been successfully employed in the discovery of novel CYP17 inhibitors, potential therapeutics for PCA.[27]

In the model generation methodology, the highest weight was assigned to the most active compound (−)-epicatechin (1; $EC_{50}$=13 μM) in the training set. This was achieved by assigning a value of 2 (which ensures that the all of the chemical features in the compound is considered for the hypothesis space) and 0 (which forces mapping of all features of the compound) in the principle and maximum omitting features columns respectively for the most active compound. A value of 1 for the principle column ensures that at least one mapping for each generated hypothesis is found, and a value of 1 for the maximum omitting features column may ensure that all but one feature must map for all other compounds (2-5) (for a detailed description of these input parameters, see the Catalyst 4.10 Tutorial[38]). All other parameters were kept at the default settings. 10 hypotheses (Hypos) were generated having scores from 36.08 to 37.81 (Table 2). The highest ranked pharmacophore hypothesis (Hypo1) generated by the HipHop approach was selected for the database search. Hypo1 was statistically best, and it maps to all the important features of the active compound and to some extent shows correlation between best fit values, conformational energies, and actual activities of the training set in comparison to other hypos (data not shown).

TABLE 2

| Hypo | Feature[a] | Rank | Direct hit mask | Partial hit mask |
|---|---|---|---|---|
| 1 | RZHH | 37.81 | 11111 | 00000 |
| 2 | ZHHH | 37.28 | 11011 | 00100 |
| 3 | ZHHH | 37.28 | 11011 | 00100 |
| 4 | ZHHH | 37.28 | 11011 | 00100 |
| 5 | RZHH | 36.95 | 11111 | 00000 |
| 6 | ZHHH | 36.45 | 11011 | 00100 |
| 7 | ZHHH | 36.45 | 11011 | 00100 |
| 8 | ZDHH | 36.19 | 01111 | 10000 |
| 9 | ZDHH | 36.19 | 01111 | 10000 |
| 10 | ZHHH | 36.08 | 11011 | 00100 |

[a]Z; Hydrophobic (HYD), H; Hydrogen bond acceptor (HBA), D; Hydrogen bond donor, R; Ring aromatic (RA)
Direct hit mask indicates (1) or (0) not a training set molecule mapped every feature.
Partial hit mask indicates whether (1) or (0) not a molecule mapped all but one feature.

Figure 3:
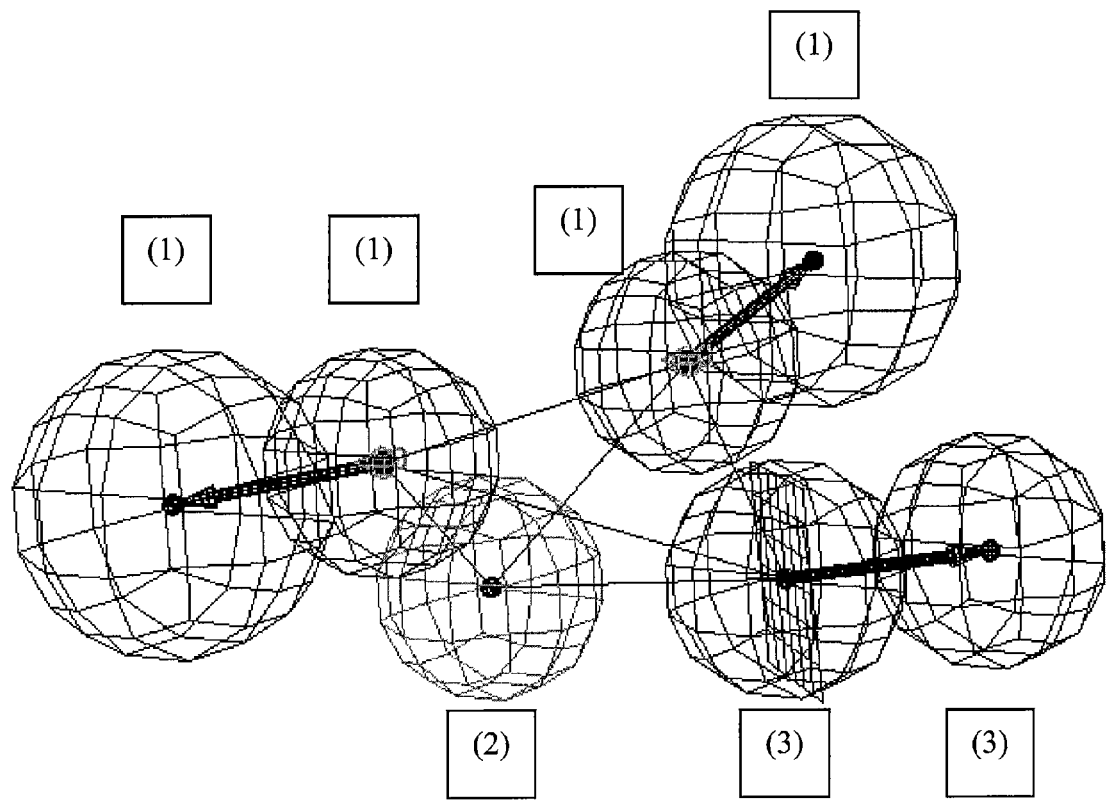
FIG. 3. Common feature-based (Catalyst/Hipop) pharmacophore model of ADRAs. The model contains four features: one hydrophobic (cyan) (2), two hydrogen bond acceptor (green) (1) and one ring aromatic (red) (3).
Figure 3A:
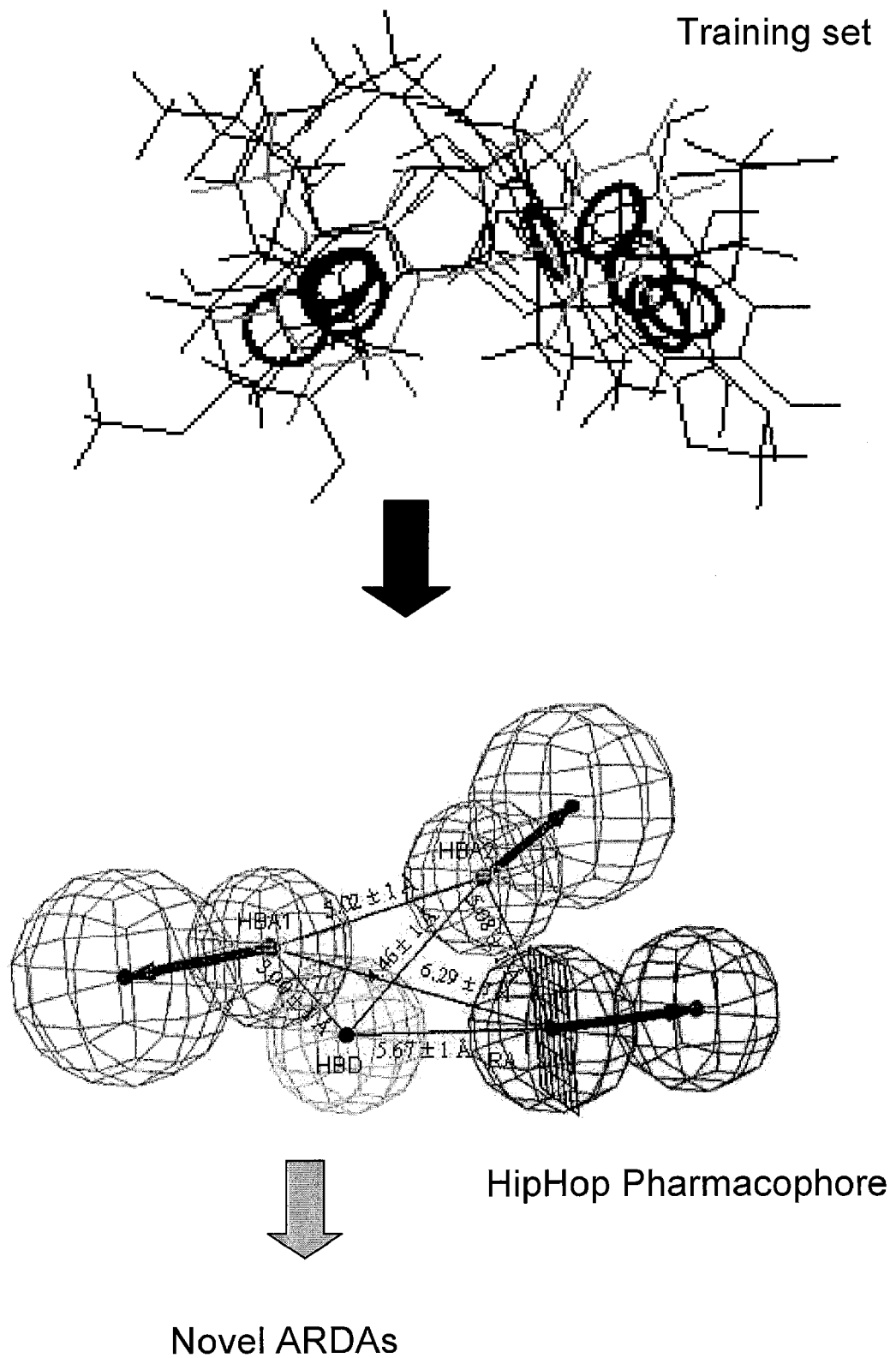
FIG. 3A. Some synthetic ARDAs discovered through generation of HipHop 3D pharmacophore modeling.
Figure 4:
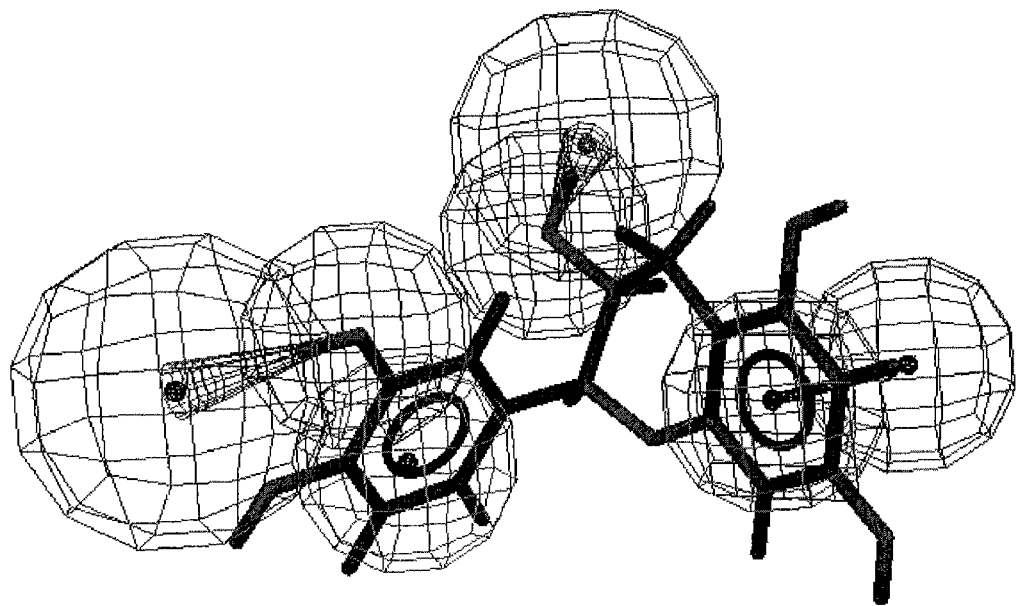
FIG. 4. The mapping of the most active molecule of training set (−) epicatechin), 1 to hypo1.
Figure 5:
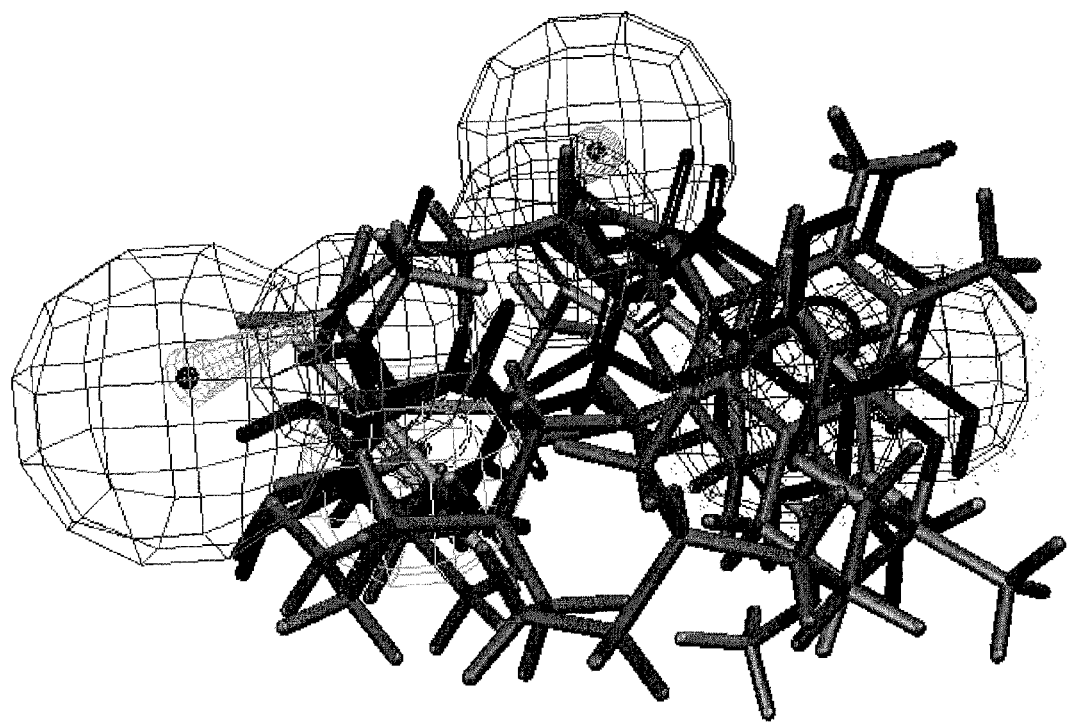
FIG. 5. Alignment of common-feature pharmacophore model with training set ADRAs.

The selected pharmacophore model contained four chemical features: one hydrophobe (HYD), two hydrogen bond acceptors (HBA1 and HBA2) and one ring aromatic (RA) (FIG. 3). The HBA-1 maps the meta-hydroxy group of the aromatic ring attached to position 2 of the benzopyran ring of epicatechin, HBA-2 maps the hydroxyl group at position 3 of the benzopyran ring, the hydrophobic feature maps the aromatic ring attached to position 2 of the benzopyran ring and ring aromatic maps the aromatic ring of benzopyran. The distance between RA and HBA1 or HBD were found to be 6.29±1 Å and 5.67±1 Å, respectively. The distance between HBA1 and HBA2 or HBD were found to be 5.02±1 Å and 3.00±1 Å, respectively. The distance between HBA2 and HBD was found to be 4.46±1 Å. FIG. 4 shows the alignment of (−) epicatechin (1) against Hypo1. This alignment represents a good match of features present in the ligand to the pharmacophore model (Fit score=3.99/4). The mapping of Hypo1 onto (−) epicatechin was performed using the "Best Fit" method in catalyst. During the fitting process, conformations on (−) epicatechin were calculated within the 20 kcal/mol energy threshold to minimize the distance between hypo features and mapped atoms of (−) epicatachin. Hypo1 has four features, and hence, the maximum fit value of any ligand alignment with this model would be 4.0. Alignment of Hypo1 with all training set compounds was performed and found to give fit scores ranging from 3.05 to 3.99 (FIG. 5). The lowest fit score (3.05) corresponds to Flufenamic acid and explains the reason for its low activity.

Figure 6:
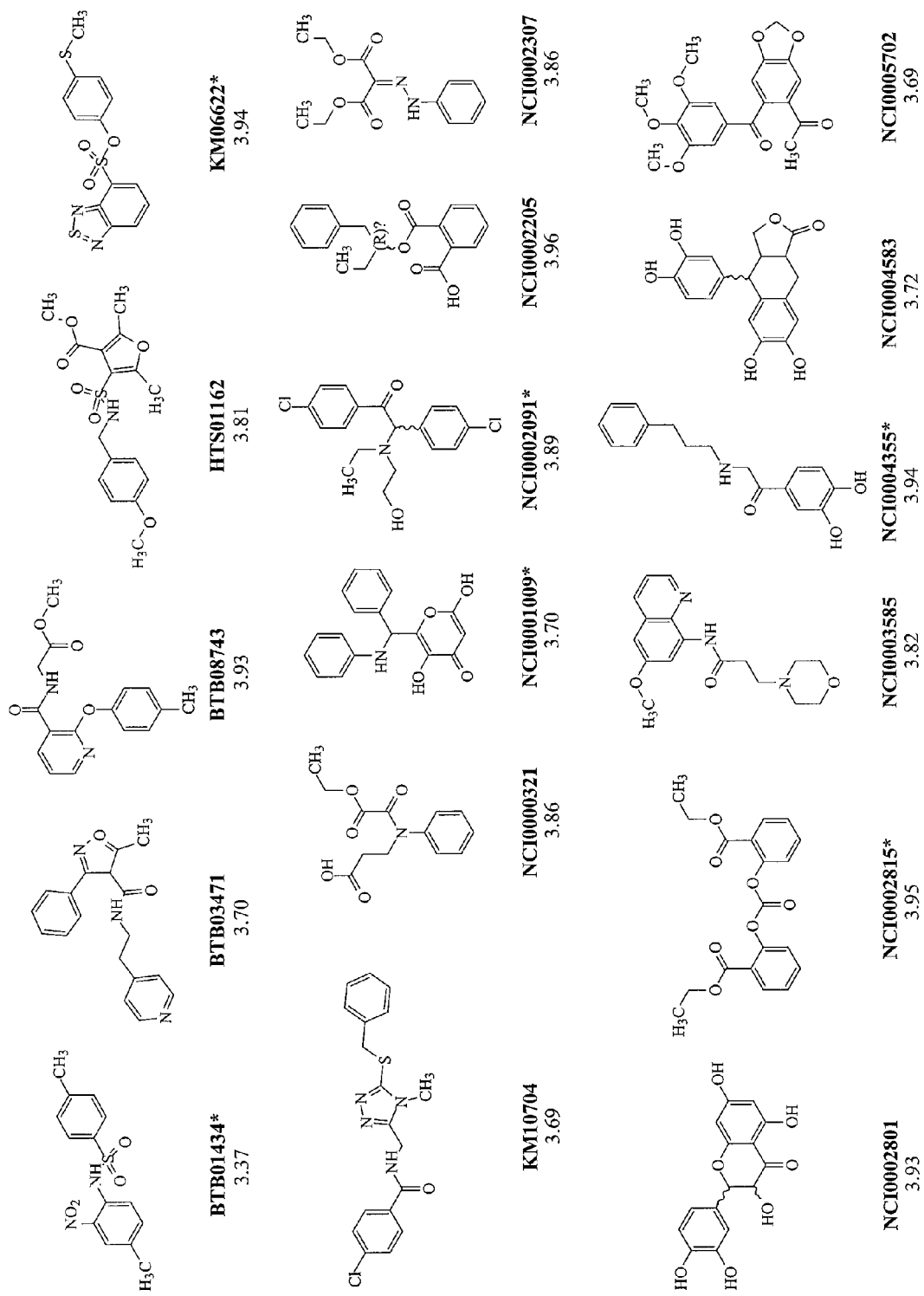
FIG. 6. Structures of some compounds (17) retrieved as "hits: from 3D searched of Catalyst formatted NCI and Maybridge Databases using the generated pharmacophore model. The star sign (*) indicates compounds (six) that found to possess significant androgen down-regulating activities.

To identify new ARDAs, Hypo1 was used as a search query against two databases: Catalyst/Maybridge 2003 (59,652 compounds) and NCI database (238,819 compounds). First, these two databases were filtered to identify molecules having molecular weight, number of rotatable-bonds and heteroatoms equal to the range of training set molecules. The search results are provided in Table 3. The hits retained for further evaluation were those with calculated fit score (of model alignment and ligand) greater than or equal to 3.05 [this is based on the lowest fit score from the alignment of the HipHop model with all five training set compounds (fit score range from 3.05 to 3.99)]. Seventeen compounds, presented in FIG. 6, were selected for further testing from the identified 41 compounds. The structures of these 17 compounds were different from that of training set and other known ARDAs. Compound NCI-0002205 possessed the highest fit value of 3.96 with the Catalyst generated pharmacophore model. The other retrieved molecules also displayed excellent fit values (3.37-3.96).

TABLE 3

| Database | DB Size | Filtered | No. of hits | % of databases | Hits with fit score > 3.05 |
|---|---|---|---|---|---|
| NCI | 59,652 | 44236 | 48 | 0.08 | 29 |
| Maybridge2003 | 238,819 | 5000 | 93 | 0.038 | 12 |

Figure 6B:
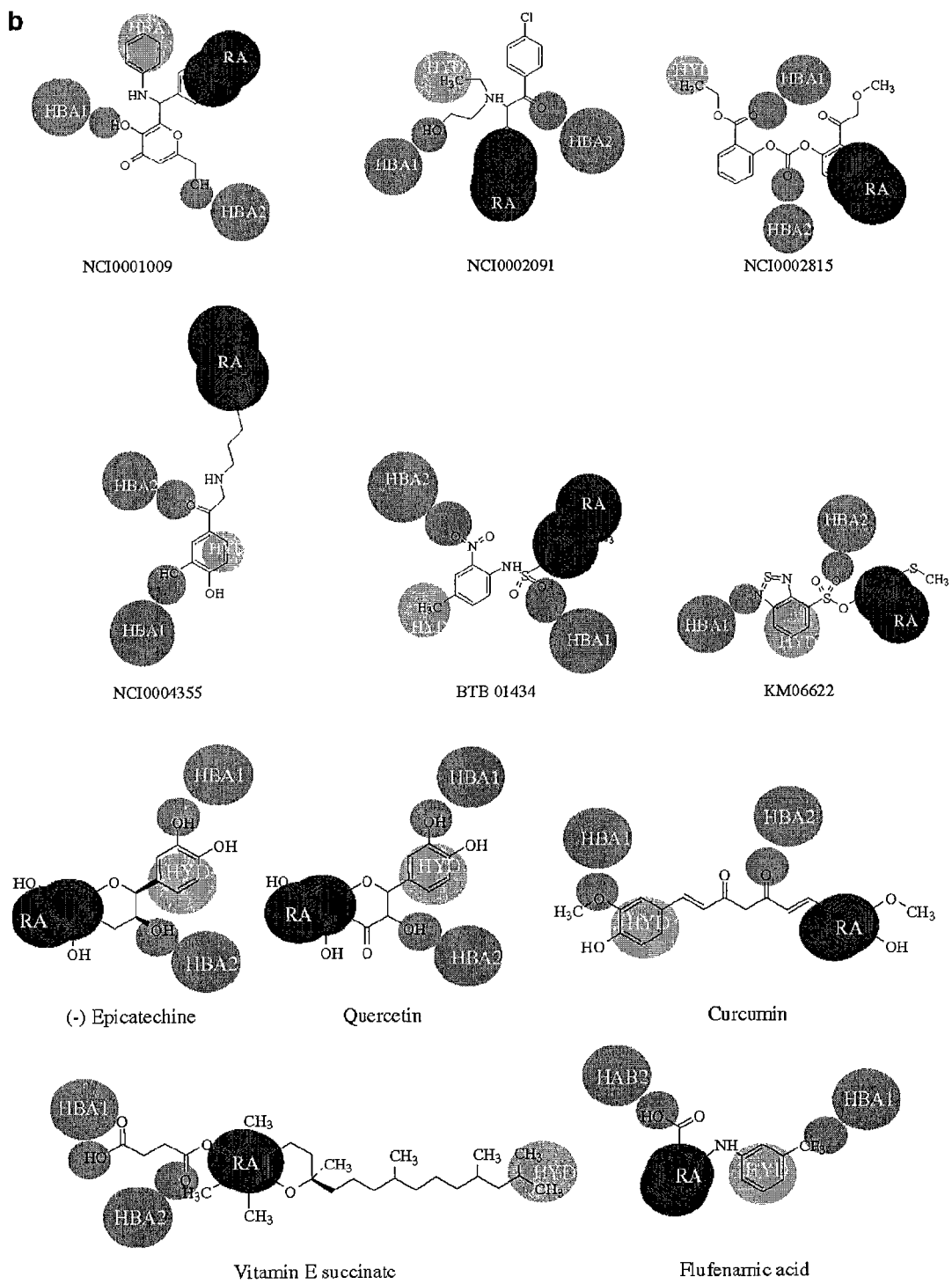
Figure 7:
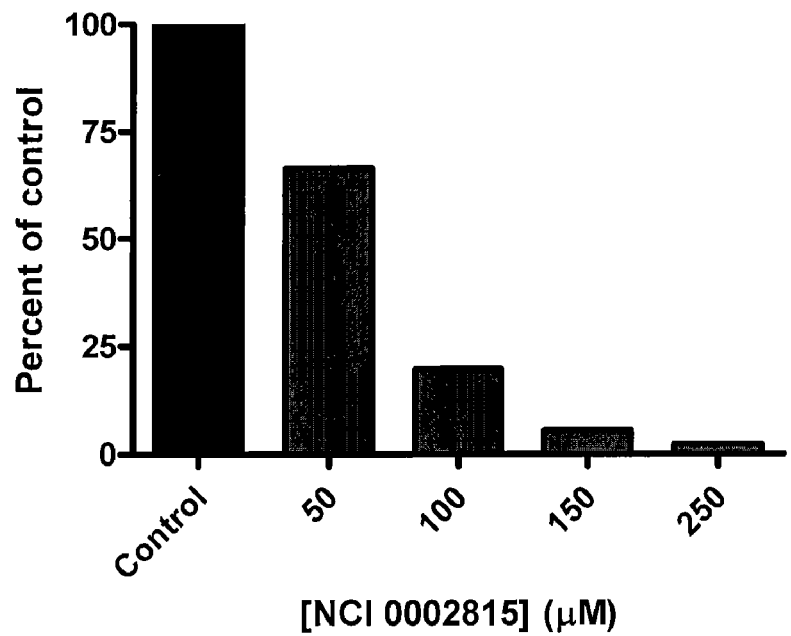

Biological studies with compounds identified using Catalyst: An initial screening of these 17 compounds at concentrations of 50 and 150 µM for their abilities to cause down-regulation of AR protein expression resulted in the identification of six active compounds. The 2D mapping of these six compounds is shown in FIG. 6b. These compounds were further evaluated to determine their $EC_{50}$ values (from dose response curves). The $EC_{50}$ values (17.5-212 µM range) as presented in Table 4 show that the compounds exhibited $EC_{50}$ values in a range similar to the range of values of the training set compounds used to generate the ARDA pharmacophore model. KM06622 was the most potent with an $EC_{50}$ value of 17.5 µM. Dose-dependent androgen receptor down-regulation activity of NCI-0002815 (determined by Western blot analysis) is shown in FIG. 7. The experiments with the other five agents gave similar plots. There is no obvious structure activity relationship (SAR) with this set of newly identified ARDAs.

TABLE 4

| Compounds | $EC_{50}$ (µM)[a] | $IC_{50}$ (µM)[b] |
|---|---|---|
| NCI-0001009 | 212 | 20.9 |
| NCI-0002091 | 39.5 | 8.31 |
| NCI-0002815 | 65.5 | 4.5 |
| NCI-0004355 | 43.5 | 26.9 |
| BTB 01434 | 76 | 39.8 |
| KM 06622 | 17.5 | >50 |

[a]EC50 values represent the ability of the compounds to down-regulate AR protein expression.
[b]IC50 values are indicative of the effect of the molecules on LNCaP cell viability. All values are indicated as percent of control.

Figure 8:
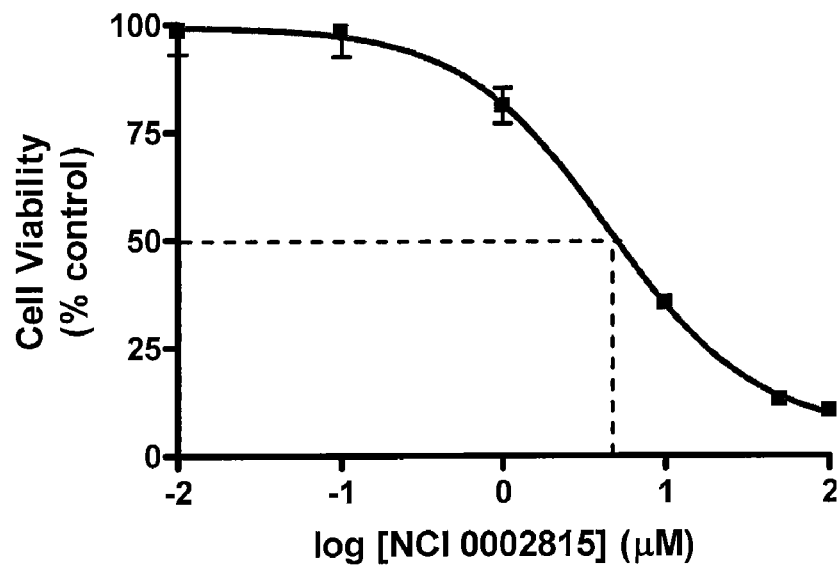

These compounds were also evaluated for their abilities to inhibit the viability of LNCaP cells. Except for KM06622, the other five compounds exhibited strong inhibition (as exemplified by their Inhibition Concentration ($IC_{50}$) values 4.5-39.8 µM) of LNCaP cell growth (Table 4). Dose-dependent curve for inhibition of human prostate LNCaP cells by NCI-0002815 is shown in FIG. 8. The experiments with the other five agents gave plots that were similar. These findings are significant because of previous reports that the well known natural products ARDAs, such as quercetin, curcumin and others inhibit the growth of human cancer cells at relatively high µM concentrations.[12,14,16] Interestingly, ARDA activity did not correspond to inhibition of cell viability in LNCaP cells.

Lead optimization of BTB01434 and further biological studies: BTB01434 (Maybridge) was used as a lead molecule to synthesize new molecules. Although this compound was not as potent as some of the others (cf. Table 4), it was chosen for its ease of modification. New compounds (6-23) were developed using the diaryl sulfonamide compound BTB01434 (FIG. 6) as a scaffold. FIG. 9 shows some exemplary embodiments of the present invention, characterized by various chemical modifications of BTB01434. It is contemplated that various other scaffold architectures may be employed that provide for a similar or at least significantly similar biological activity as that of the current embodiment. Including new BTB01434 analogs, including diaryl sulfonamide analogs bearing various substituents on the phenyl rings (series A), aryl amide analogs (series B), and amine analogs (series C). These new compounds were evaluated for cell growth inhibition in two human prostate cancer cell lines, (LNCaP and PC-3) by MTT assay. Based on the structures and anti-prostate cancer activities of the new compounds, a structure-activity relationship (SAR) was formulated. This SAR clearly reveals the structural features of new compounds responsible for the growth inhibitory activities in human prostate cancer cells.

The compounds described in this study were prepared following straightforward chemistry as outlined in Schemes 1a-e (series A), Scheme 2 (series B), and Scheme 3 (series C). Compounds 6-9, 11 and 13, were synthesized by refluxing appropriate substituted aryl amines with the corresponding aryl sulfonyl chlorides in pyridine (Scheme 1a).[29] The carboxylic acid containing compounds 10 and 12 were synthesized by treatment of 2-amino-5-methylbenzoic acid in aqueous $Na_2CO_3$ solution at 60° C. followed by reaction with appropriate benzene sulfonyl chloride at 80° C. (Scheme 1b).[30] Treatment of the cyano compound 13 with sodium azide and ammonium chloride in DMF at 120° C. afforded the corresponding tetrazole 14 (Scheme 1C).[23,4] Compounds 15-17 were synthesized by simply triturating appropriate substituted anilines with the corresponding aromatic sulfonyl chlorides (Scheme 1d).[24,4] The tertiary sulfonamide compound 18 was obtained by treatment of 11 with methyl iodide in the presence of 1-butyl-3-methyl imidazolium hexafluoro phosphate at room temperature (Scheme 1e).[25,4] Reaction of appropriate aryl amine with aryl aldehyde in presence of triethyl amine afforded the benzamide 19 (Scheme 2).[26,4] Finally, the aryl amines 21 and 23 were obtained by reducing intermediate imines 20 and 22 respectively with sodium borohydride. The intermediate imines (20 and 22) were prepared by condensation of appropriate aryl amines and benzaldehydes (Scheme 3).[27B] All compounds were properly characterized by physical and spectroscopic analyses. However, with regards to compound 10, we observed a significant difference in the melting point reported for this compound in the literature (130° C.) from that obtained in this study (197-198° C.). The spectral data ('H NMR and HRMS) confirm with certainty the integrity of this compound. Except compounds 9, 12, 13 and 14, all other compounds described in the study have previously been reported.[21,25, 28-35]

Scheme 1

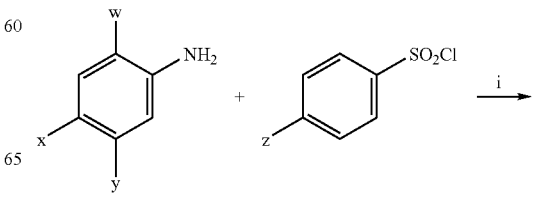

a

15
-continued

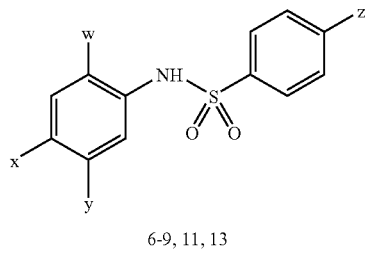

6-9, 11, 13

| a | w | x | y | z |
|---|---|---|---|---|
| 6 | NO$_2$ | H | H | CH$_3$ |
| 7 | NO$_2$ | H | H | H |
| 8 | NO$_2$ | CH$_3$ | H | H |
| 9 | NO$_2$ | CH$_3$ | H | F |
| 11 | H | CH$_3$ | H | CH$_3$ |
| 13 | CN | H | CH$_3$ | F |

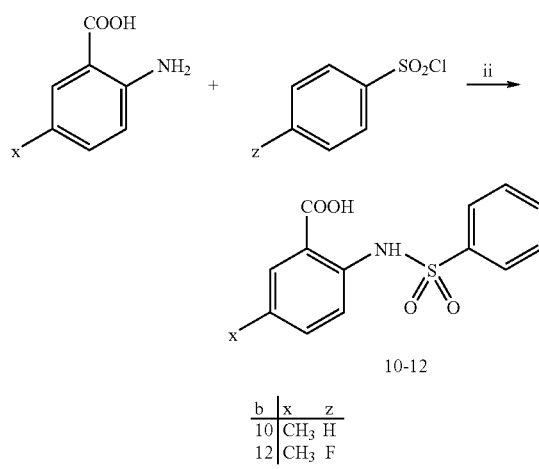

10-12

| b | x | z |
|---|---|---|
| 10 | CH$_3$ | H |
| 12 | CH$_3$ | F |

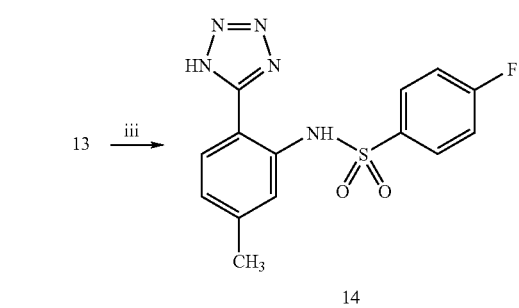

14

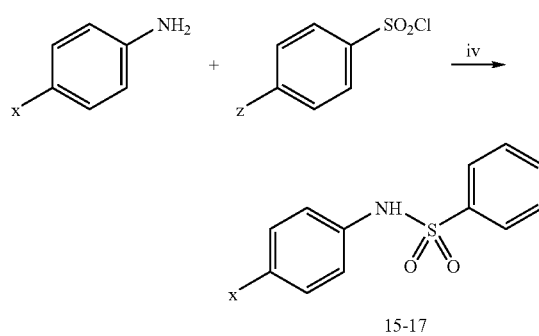

15-17

| d | x | z |
|---|---|---|
| 15 | CH$_3$ | H |
| 16 | H | CH$_3$ |
| 17 | H | H |

16
-continued

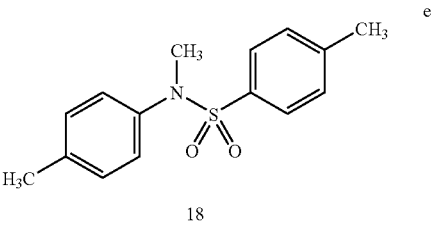

18

Reagents and conditions:
(i) Pyridine, reflux, 125° C. 6 hr;
(ii) Na$_2$CO$_3$, reflux, 80° C., 6 hr;
(iii) NH$_4$Cl, NaN$_3$, DMF, 120° C., 20 hr;
(iv) NaHCO$_3$, rt, 5-10 min;
(v) CH$_3$I, 1-butyl-3-methyl imidazolium hexafluoro phosphate, rt, 2 hr.

Scheme 2

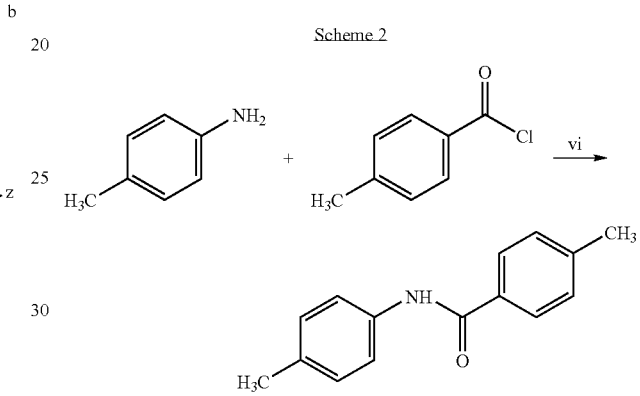

19

Reagents and conditions: (vi) TEA, EtOAc, rt, 12 h.

Scheme 3

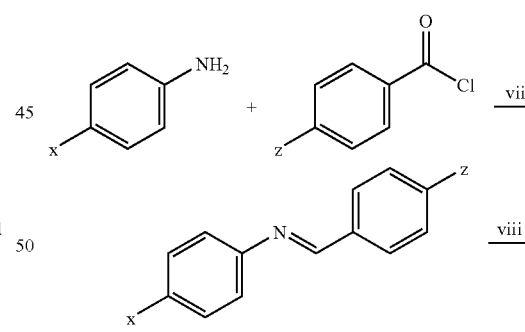

20 x, z = CH$_3$
22 x = CH$_3$, z = H

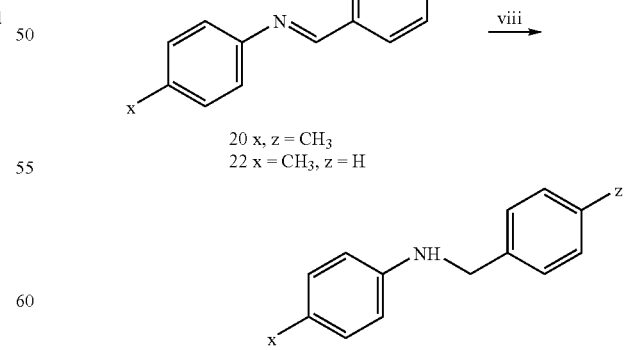

21 x, z = CH$_3$
23 x = CH$_3$, z = H

Reagents and conditions: (vii) EtOH, reflux, 12 h; (viii) MeOH, NaBH$_4$, rt, 10 min.

Figure 10:
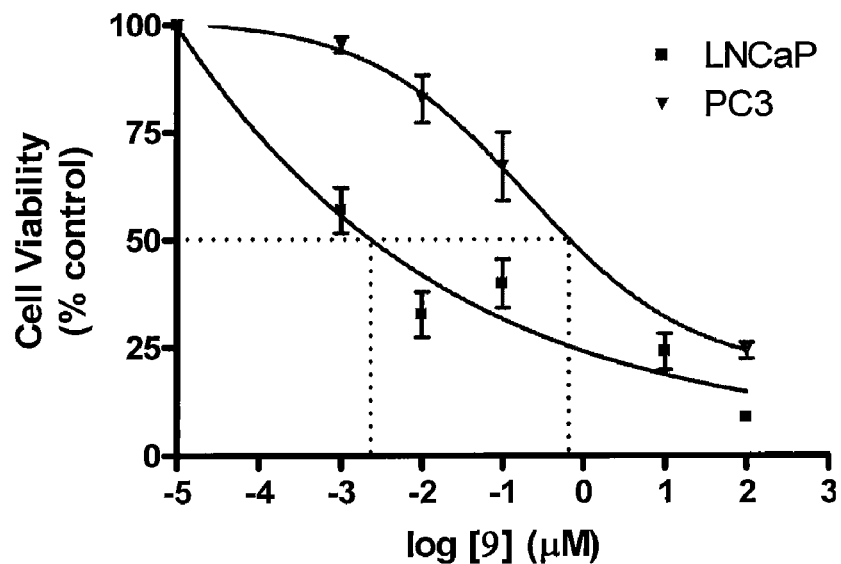
FIG. 10. The effect of 9 (a) and 11 (b) on LNCaP and PC3 cell viability. Data is represented as mean±SE.
Figure 10:
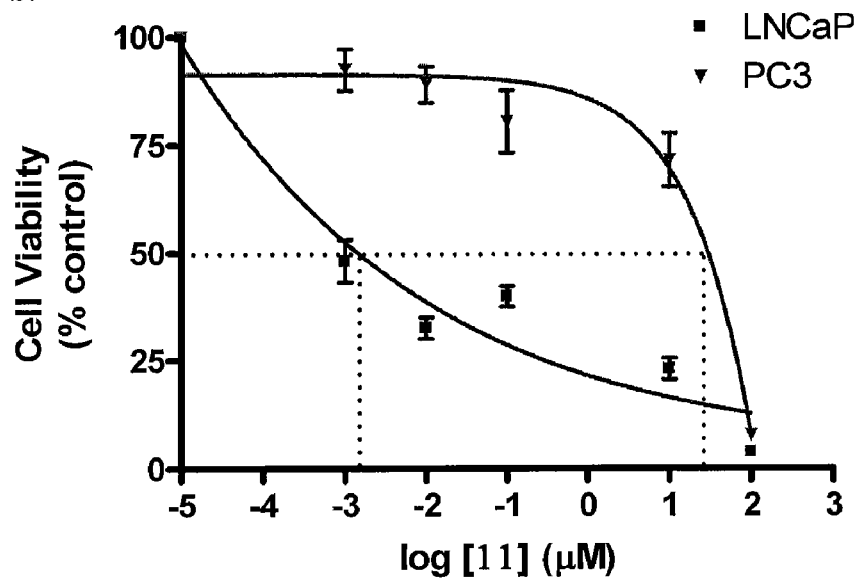

Inhibition of prostate cancer cell proliferation and SAR: The exemplary compounds were then tested for their ability to inhibit cell viability in both the LNCaP (mutant AR) and PC-3 (AR null) cell lines (Table 5). All six of the new compounds (6-11) displayed $IC_{50}$ values 500-27,000 fold lower than the parent compound, BTB01434 in LNCaP cells, and may be found to be less active against PC-3 cells. Compound II was found to be the most potent compound in the LNCaP cells, yet may not exhibit similar potency in the PC-3 cells. On the other hand, compound 9 was highly potent in both the LNCaP and PC-3 cell lines (Table 5, and FIG. 10).

ture/activity relationship (SAR) around the sulfonamide moiety. An SAR was developed with BTB01434 and compounds 6-11 using human prostate LNCaP cell growth inhibition assay. Firstly, examination of the growth inhibitory data reveals that substituting any of the three aryl substituents (i.e., $CH_3$ of ring B and $CH_3$ or $NO_2$ of ring A) with either H, F or $CO_2H$ led to interesting SAR information. Clearly, these substitutions led to excellent enhancement (480- to 27.000-fold) in growth inhibitory activities. Substitution of $CH_3$ of ring B with H resulted in the largest enhancement of activity ($GI_{50}$ from 39,800 nM of BTB01434→2.95 nM of 8), while

TABLE 5

A

| Cmpd | w | x | y | z | Cytotoxicity $GI_{50}$ (nM) LNCaP | $GI_{50}$ (nM) PC-3 | ARDA $EC_{50}$ (μM) |
|---|---|---|---|---|---|---|---|
| BTB01434 | $NO_2$ | $CH_3$ | H | $CH_3$ | 39,800 | 43,670 | 76.0 |
| 6 | $NO_2$ | H | H | $CH_3$ | 83.00 | 50,110 | >150 |
| 8 | $NO_2$ | $CH_3$ | H | H | 2.95 | 60,250 | NT |
| 7 | $NO_2$ | H | H | H | 14.08 | 22,900 | NT |
| 9 | $NO_2$ | $CH_3$ | H | F | 2.34 | 850.0 | NT |
| 11 | H | $CH_3$ | H | $CH_3$ | 1.45 | 30,200 | 150 |
| 10 | COOH | $CH_3$ | H | H | 18.20 | 1,350 | NT |
| 12 | COOH | $CH_3$ | H | F | 10,700 | >100,000 | NT |
| 13 | CN | H | $CH_3$ | F | 30,200 | ~100,000 | NT |
| 14 | 1H-tetrazole | H | $CH_3$ | F | >100,000 | >100,000 | NT |
| 15 | H | $CH_3$ | H | H | 21,300 | 13,800 | NT |
| 16 | H | H | H | $CH_3$ | 24,000 | 38,900 | NT |
| 17 | H | H | H | H | 53,500 | >100,000 | NT |

B

| Cmpd | Structure | Cytotoxicity $^a$LNCaP | $GI_{50}$ (nM) $^a$PC-3 | ADRA (μM) |
|---|---|---|---|---|
| 18 | (structure: sulfonamide with N-CH3, two tolyl rings) | 89,150 | 44,660 | NT |
| 19 | (structure: benzamide NH, two tolyl rings) | 54,950 | 26,920 | NT |

C.

(structure: two para-substituted phenyl rings connected by X)

| Cmpd | x | X | z | Cytotoxicity LNCaP | $GI_{50}$ (nM) PC-3 | ADRA (μM) |
|---|---|---|---|---|---|---|
| 20 | $CH_3$ | N=CH | $CH_3$ | NT | NT | NT |
| 21 | $CH_3$ | HN—$CH_2$ | $CH_3$ | 19,050 | 29,510 | NT |
| 22 | $CH_3$ | N=CH | H | NT | NT | NT |
| 23 | $CH_3$ | HN—$CH_2$ | H | >100,000 | 52,400 | NT |

$^a$Values are means of three independent experiments, SEM = ±10%, NT-Not tested. Compounds 15 and 17 were unstable under the assay conditions.

The exemplary structural embodiments of the current invention, characterized as resulting from chemical modifications of BTB01434, may enable the evaluation of the strucreplacement of the methyl group of ring A with H also yielded excellent enhancement of activity ($GI_{50}$ from 39,800 nM of BTB01434→83.0 nM of 6). Interestingly, removal of both CH$_3$ groups from rings A and B resulted in compound 7, with GI$_{50}$ of 14.8 nM, a value 5-fold less potent than 8 and 5.6-fold more potent than 6. Introduction of the electron withdrawing fluorine in ring B of 8 yielded compound 9 (GI$_{50}$=2.34 nM) with no significant change in activity. The strong electron withdrawing NO$_2$ group appears to cause decrease in activity, because its replacement with H led to exquisite enhancement of activity (GI$_{50}$ from 39,800 nM of BTB01434→1.45 nM for 11). However, its replacement with the moderate electron withdrawing CO$_2$H in the absence of the CH$_3$ group of ring B resulted in a 6-fold decrease in activity (GI$_{50}$ from 2.95 of 8→18.2 nM for 10). Introduction of a p-fluoro group in ring B of compound 10 resulted in 12 with a drastic decrease in activity. In addition, as shown for compounds 13 and 14, replacement of the nitro group with either CN or 1H-tetrazole also afforded deleterious effects on inhibitory activity.

We further investigated the effects of the methyl substituents on rings A and B of our most potent compound II (GI$_{50}$=1.45 nM). As shown in compounds 15, 16 and 17, removal of either or both methyl groups resulted in drastic loss of activity. Clearly, the effects of the methyl groups in 11 are in contrast to their effects on the potency of compound 6 described above. To probe the contribution of the —NH— group, we synthesized compound 18, an N-methyl derivative of 11. Introduction of the N-methyl group resulted in drastic decrease in activity (GI$_{50}$ from 1.45 nM of 11→89,150 nM of 18). Furthermore, replacement of the sulfonamide linker (—SO$_2$NH—) with two other types of linkers, that is, amide (19), and amines (21 and 23) resulted in significant loss of activity.

As stated above, some compounds, such as 9 and 10 exhibited potent inhibition of PC-3 cell growth which suggest that they might have mechanisms of action other than interrupting the AR signaling pathway in human prostate cancer cells. It was of interest to evaluate the effects of selected compounds on AR protein expression and also on their abilities to bind to and cause transactivation of the AR. Therefore, the novel compounds of the current invention may be useful with various types of cancer cells and not be specifically limited to prostate cancer cells.

Effects of compounds 6 and 11 on AR protein expression: For comparison purposes, the most and least effective compounds in the LNCaP cells, compounds 11 and 6, respectively, were examined for their AR down-regulating activity. Both of these compounds were not effective at decreasing AR protein expression since they each caused less than 50% AR protein expression at relatively high concentrations (150 µM). These results suggest the growth inhibitory effects of compounds 6-11 may be due to properties not related to AR down-regulation.

Figure 11:
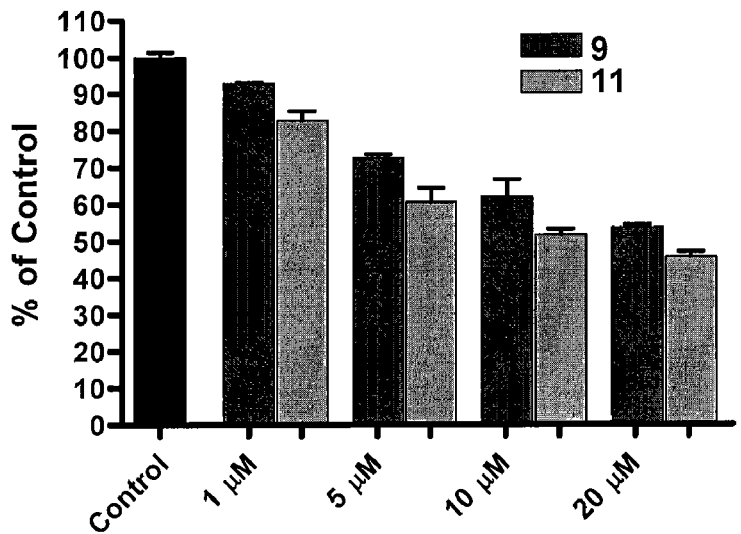
FIG. 11. Dose response for the competition of 9 and 11 for AR biding to 3H-R1881 in a) LNCaP cells and in b) PC-3-AR transfected cells.
Figure 11:
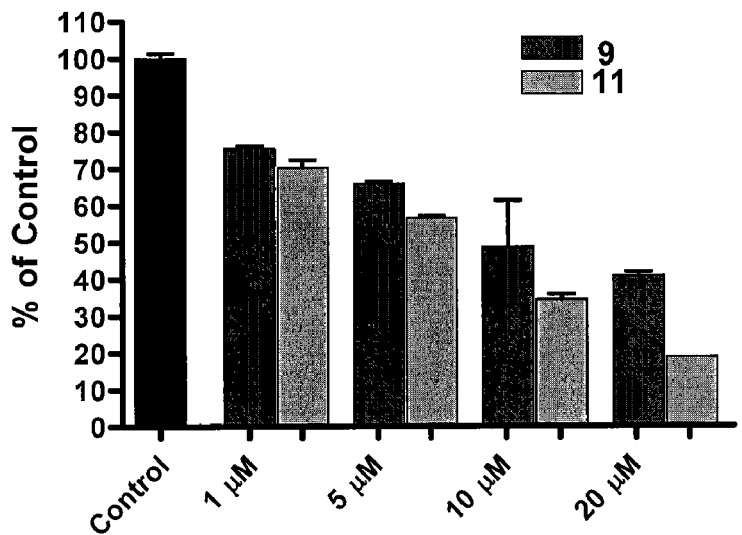

LNCaP and PC-3 AR Androgen Receptor Binding and AR-Mediated Transcription Studies: Competitive androgen binding studies were carried out utilizing the labeled synthetic androgen [$^3$H]-R1881 in androgen dependent LNCaP cells that express a mutated AR, and androgen independent PC-3 cells stably transfected with the wild-type AR (PC-3-AR) as previously described.[10] In this assay, we selected the most active compound II in LNCaP cells (IC$_{50}$=1.45 nM) and 9 that was active in both LNCaP (IC$_{50}$=2.34 nM) and PC-3 (IC$_{50}$=850 nM) cell lines. In both cell lines, compounds 9 and 11 were able to effectively compete with labeled R1881 in a dose-dependent fashion (FIG. 11). In PC-3-AR cells compound II reduced [$^3$H]-R1881 binding by 65% and 80% at 10 µM and 20 µM, respectively. However, compound 11 favored binding to the wild-type AR over the mutated receptor, with an approximately 20% greater inhibition of [$^3$H]-R1881 binding to the wild-type AR at 10 µM and above. Compound 9 reduced [$^3$H]-R1881 binding by 50% and 65% at 10 µM and 20 µM, respectively, and was equipotent in both cell lines.

Figure 12:
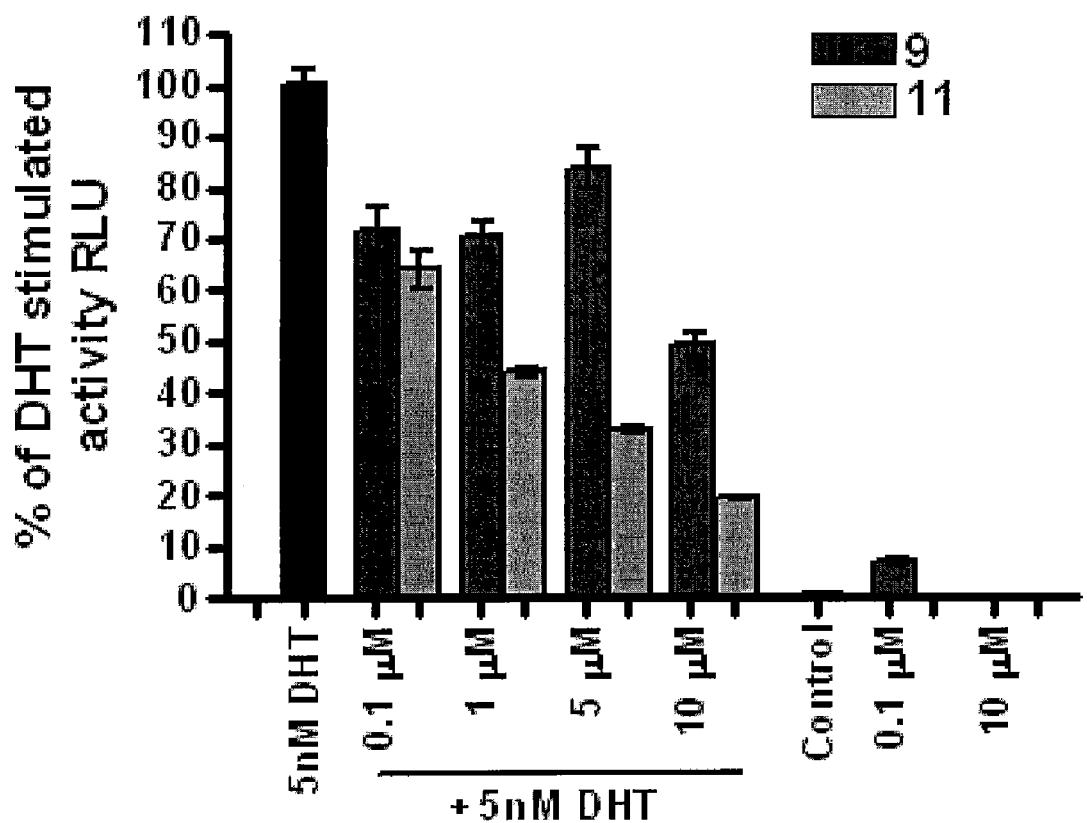
FIG. 12. The effects of 9 and 11 and casodex on transcriptional activity of luciferase mediated through LNCaP-AR in LNCaP-ARR2-lu prostate cancer cells. Cells in steroid-free medium were treated with vehicle, or increasing concentrations of either 9 or 11 with and without 5 nM DHT for 18 h. Cells were then assayed for luciferase activity using a know assay.[10]

To determine if the compounds act as AR agonists or antagonists, androgen regulated transcriptional activation studies were performed in LNCaP cells transiently transfected with the probasin luciferase reported construct ARR2-Luc. The results are presented in FIG. 12. 5 nM DHT stimulated luciferase activity approximately 200 fold. Compound II alone had no effect on luciferase activity at 0.1 and 10 µM concentrations. Compound 9 did not increase luciferase expression at 10 µM, however there was a slight increase at 0.1 µM. In the presence of DHT, compounds 9 and 11 reduced luciferase expression by 50% and 80% at 10 µM, respectively. Taken together, these results suggest that both compounds do not possess AR agonistic activity and may be considered as strong, pure androgen receptor antagonists. It is relevant to point out that the potency of compound 5 is similar to potencies of our steroidal CYP17/antiandrogens and casodex, a clinically used anti-androgen that were previously tested by us in a similar assay[36] as that used in this study.[10] Although we did not test the compounds with PC-3AR/LU cells, which express wild-type AR, it is likely that they may also behave in a similar fashion. In general, these agents interacted strongly with both AR types, an indication that the compounds may be useful for the treatment of patients with tumors expressing either wild-type or mutated AR.

The biological studies with these lead-modified compounds (6-19, 21 and 23) suggest that their PC growth inhibitory activities are not due to effects on AR expression, but in some cases may involve AR antagonistic properties. However, either with or without anti-androgenic activities, these compounds have the potential to treat both androgen-dependent and androgen-refractory PCA. The antiproliferative properties of the novel diaryl sulfonamides of the current invention in both LNCaP and PC-3 cell lines suggest that the compounds are capable of interacting with multiple cellular targets.

The current invention provides for the identification of androgen receptor down-regulating agents (ARDAs). This may be accomplished by generating a three dimensional pharmacophore model based on a training set of five well-known ARDAs. The model containing one hydrophobic group, one ring aromatic group, and two hydrogen bond acceptors identified 48 and 93 compounds from the NCI (59,652 compounds) and Maybridge (238,819 compounds) databases, respectively. The current invention identified that of six small molecules that were experimentally confirmed as ARDAs they also exhibited significant human prostate cancer LNCaP proliferation inhibitory activities. Lead optimization of one of these compounds afforded sulfonamide compounds that are extremely potent inhibitors of LNCaP cell growth and some are strong inhibitors of PC-3 cell growth as well. The novel compounds of the current invention possess new scaffolds and because of their exceptional PCA growth inhibitory potencies and high synthetic feasibility may allow for the development of treatment(s) of prostate cancer.

Methods and Materials

Androgen-dependent LNCaP cells were obtained from American Type Culture Collection (Rockville, Md., USA). Cells were maintained in RPMI 1640 medium supplemented with 10% fetal bovine serum (Atlanta Biologicals, Lawrenceville, Ga., USA) and 1% penicillin/streptomycin. Cells were grown as a monolayer in T75 or T150 tissue culture flasks in a humidified incubator (5% CO$_2$, 95% air) at 37° C.

For immunoblot detection of the AR, LNCaP cells were cultured as described above in T25 flasks. Cells were treated with various concentrations of ARDAs and whole cell lysates were prepared using lysis buffer containing 0.1M Tris, 0.5% Triton X-100, and protease inhibitor. Protein content was determined using the Bradford Assay (Bio-Rad, Hercules, Calif., USA). Protein was subjected to SDS-PAGE (10% acrylamide) and transferred onto nitrocellulose membrane. The blots were blocked overnight in 5% nonfat milk in PBS-T buffer at 4° C. Monoclonal antibody was used against the AR (AR441; sc-7305; Santa Cruz Biotechnology, Santa Cruz, Calif.; 1:500 dilution) at room temperature for one hour. Membranes were then incubated with a goat anti-mouse IgG secondary antibody conjugated to horseradish peroxidase (Bio-Rad cat #170-6516; 1:2000 dilution) at room temperature for one hour. Blots were rinsed with PBS-T between each step and specific bands were visualized by enhanced chemiluminescence (ECL; Amersham Biosciences, Arlington Heights, Ill., USA). Equivalent loading of samples was determined by reprobing membranes with $\beta$-actin (Calbiochem, USA). Protein expression was normalized to $\beta$-actin.

Cell Growth Inhibition (MTT Colorimetric Assay)

LNCaP cells were seeded in 24 well plates (Corning Costar) at a density of $2 \times 10^4$ cells per well per 1 mL of medium. Cell were allowed to adhere to the plate for 24 hours and then treated with different concentrations of ARDAs dissolved in DMSO. Cells were treated for five days with renewal of ARDA and media on day 3. On the fifth day, medium was renewed and 100 µL of MTT (3-(4,5-dimethylthiazol-2-yl)-2,5-diphenyl-2H-tetrazolium bromide from Sigma) solution (0.5 mg MTT/mL of medium) was added to the medium such that the ratio of MTT:medium was 1:10. The cells were incubated with MTT for 2 hours. The medium was then aspirated and 500 µL of DMSO was added to solubilize the violet MTT-formazan product. The absorbance at 560 nm was measured by spectrophotometry (Victor 1420 multilabel counted, Wallac). For each concentration of ARDA there were triplicate wells in each independent experiment. $IC_{50}$ values were calculated by nonlinear regression analysis using GraphPad Prism software.

Competitive Androgen Receptor (AR) Binding and Luciferase Transactivation Assays:

These assays were performed as previously described.[10]

Computational Methods

All molecular modeling studies were performed using Catalyst 4.10[38] installed on Silicon Graphics $O_2$ work-station equipped with a 300 MHz MIPS R5000 processor (128 MB RAM) running the Irix 6.5 operating system.

All structures were generated using 2D/3D editor sketcher and minimized to the closest minimum using the CHARMm-like force field implemented in the program.[39] Regarding the asymmetric centers of all the compounds, as we tested ss isomer of (−) epicatachin we assigned ss for epicatachin, where for quercetin and vitamin E succinate, it was arbitrarily decided to assign 'undefined' chirality, allowing the pharmacophore model to choose which configuration of the asymmetric carbon atoms is the most appropriate. A stochastic research coupled to a poling method[40] was applied to generate conformers for each compound by using 'Best conformer generation' option with a 20 kcal/mol energy cutoff (20 kcal/mol maximum compared to the most stable conformer).

The pharmacophore-based investigation of ADRAs involved using the catalyst/HipHop program to generate feature-based 3D pharmacophore alignments.[41,42] This was performed in a three step procedure:[43] (a) a conformation model for each molecule in the training set was generated; (b) each conformer was examined for the presence of certain chemical features; (c) a three-dimensional configuration of chemical features common to the input molecules was determined.

Catalyst provides a dictionary of chemical features found to be important in drug-enzyme/receptor interactions. These are hydrogen bond donors (HBD), hydrogen bond acceptors (HBA), hydrophobic group (HYD), ring aromatic (RA) and positive (PI) and negative ionizable (NI) groups. For the pharmacophore modeling runs, common features selected for the run were ring aromatic (R), hydrogen bond donor (D), hydrogen bond acceptor (H), hydrophobic group (Z) and negative ionizable group (N). The default HBA of the feature dictionary which recognizes N, O, and S as hydrogen bond acceptors was modified to include 'F', as Flufenamic acid (molecule 3 of Table 1) contains trifluoromethyl group based on electronegativity differences, 'F' is also thought to act as hydrogen bond acceptor.

Chemistry: General procedures and techniques were identical with those previously reported.[29,30] $^1$H NMR spectra were recorded in $CDCl_3$ (unless mentioned) with $Me_4Si$ as an internal standard using Varian Inova 500 MHz spectrometer operating at 150 MHz. High-resolution mass spectra (HRMS) were determined on a 12T Bruker FTICR-MS with an Apollo II ion source, by positive ion electrospray. Low-resolution mass spectra (LRMS) were determined on a Finnegan LCR-MS. Infrared spectra were recorded on a Perkin-Elmer 1600 FTIR spectrometer using solutions in $CHCl_3$. Melting points (mp) were determined with fisher Johns melting point apparatus and are uncorrected. As a criterion of purity for key target compounds, we provided high-resolution mass spectral data with HPLC chromatographic data indicating compound homogeneity. All the precursors required for synthesis were purchased from Aldrich.

[(4-Methylphenyl)sulfonyl](2-nitrophenyl)amine (Compound 6). To a solution of 2-nitroaniline (1 g, 7.24 mmol) in dry pyridine (4 mL) at 125° C. was added 4-methyl-benzenesulfonyl chloride (1.38 g, 7.24 mmol) over a period of three minutes, and the reaction mixture was stirred for 6 h at 125° C., at which time the reaction was complete as determined by TLC. The reaction mixture was concentrated under reduced pressure and the concentrate was poured into of ice cold water (300 mL). The resulting reddish brown solid was filtered, washed with water and dried to give 6 (1.12 grams, 52.9%). Crystallization from EtOH gave (0.82 g) yellow needle shaped crystals, mp 112-113° C. (lit[29] 111-112° C.); IR ($CHCl_3$) 3289, 1530, 1349, 1170, 1147, 757 cm$^{-1}$; $^1$H NMR (500 MHz, $CDCl_3$) $\delta$ 2.38 (s, 3H, $CH_3$), 7.14-8.11 (m, 7H, aromatic), and 9.84 (s, 1H, NH). HRMS calcd 315.0409 ($C_{13}H_{12}N_2O_4S.Na^+$), found 315.0407.

(2-Nitrophenyl)(phenylsulfonyl)amine (Compound 7). The method followed that described for compound 6 but using 2-nitroaniline (1 g, 7.24 mmol) and benzenesulfonyl chloride (1.28 g, 7.24 mmol) in dry pyridine (4 mL) to give 7 (1.54 g, 66.51%). Crystallization with EtOH gave (1.34 g) yellow crystals, mp 102° C. (lit[29] 101-102° C.); IR ($CHCl_3$) 3286, 1530, 1350, 1172, 1147, 686 cm$^{-1}$; $^1$H NMR (500 MHz, $CDCl_3$) $\delta$ 7.16-8.11 (m, 9H, aromatic), and 9.85 (s, 1H, NH). HRMS calcd 301.0253 ($C_{12}H_{10}N_2O_4S.Na^1$), found 301.0257.

(4-Methyl-2-nitrophenyl)(phenylsulfonyl)amine (Compound 8). The method followed that described for compound 6 but using 2-nitro-4-methylaniline (1 g, 6.57 mmol) and benzenesulfonyl chloride (1.17 g, 6.57 mmol) in dry pyridine (4 mL), to give 8 (1.22 g, 63.48%). Crystallization with EtOH gave (1.1 g) yellow needle shaped crystals, mp 95-96° C. (lit[31] 101-102° C.); IR ($CHCl_3$) 3286, 1530, 1350, 1172, 1147, 686 cm$^{-1}$; $^1$H NMR (500 MHz, $CDCl_3$) $\delta$ 2.34 (s, 3H, $CH_3$), 7.26-7.87 (m, 8H, aromatic) and 9.62 (s, 1H, NH). HRMS calcd 315.0409 ($C_{13}H_{12}N_2O_4S.Na^+$), found 315.0412.

[(4-Fluorophenyl)sulfonyl](4-methyl-2-nitrophenyl) amine (Compound 9). The method followed that described for compound 6 but using 2-nitro-4-methylaniline (1 g, 6.57 mmol) and 4-fluoro-benzenesulfonyl chloride (1.4 g, 6.57 mmol) in dry pyridine (4 mL), to give 9 (1.7 g, 83.33%). Crystallization with EtOH gave (1.4 g) white crystals, mp 109-112° C.; IR (CHCl$_3$) 3289, 1533, 1351, 1173, 1156, 661 cm$^{-1}$; $^1$H NMR (500 MHz, CDCl$_3$) δ 2.35 (s, 3H, CH$_3$), 7.10-7.89 (m, 7H, aromatic) and 9.59 (s, 1H, NH). HRMS calcd 333.0315(C$_{13}$H$_{11}$FN$_2$O$_4$S.Na$^+$), found 333.0314.

5-Methyl-2-[(phenylsulfonyl)amino]benzoic acid (Compound 10). To a solutions of 2-amino-5-methyl-benzoic acid (0.2 g, 1.32 mmol), sodium carbonate (0.34 g, 3.17 mmol) in water (2 mL) at 60° C. was added benzenesulfonyl chloride (0.28 g, 1.58 mmol) over a period of two minutes, and the reaction mixture was stirred for 6 h at 80° C., at which time the reaction was complete as determined by TLC. The reaction mixture was cooled to room temperature and acidified with 6N HCl solution and resulting cream colored solid was filtered, washed with water and dried to give 10 (0.39 grams, 98.7%). Crystallization from EtOH gave (0.22 g) white needle shaped crystals, mp 197-198° C. (lit$^{32}$ 130° C.); IR (nujol) 3202, 1669, 1341, 1167, 1149, cm$^{-1}$. $^1$H NMR (500 MHz, DMSOD$_6$) δ 2.16 (s, 3H, CH$_3$), 7.30-7.71 (m, 8H, aromatic) and 10.88 (br, 1H, COOH). HRMS calcd 314.0457 (C$_{14}$H$_{13}$NO$_4$S.Na$^+$), found 314.0460.

(4-Methylphenyl)[(4-methylphenyl)sulfonyl]amine (Compound II). The method followed that described for compound 6 but using p-toluedine (0.5 g, 4.66 mmol) and 4-methyl-benzenesulfonyl chloride (0.89 g, 4.66 mmol) in dry pyridine (2 mL), to give 11 (1.0 g, 82%). Crystallization with EtOH gave (0.73 g) white crystals, mp 114-115° C. (lit$^{33}$ 116° C.); IR (CHCl$_3$) 3256, 1510, 1332, 1160, 766$^{-1}$; $^1$H NMR (500 MHz, DMSOD$_6$) δ 2.18 (s, 3H, CH$_3$), 2.33 (s, 3H, CH$_3$), 6.94-7.60 (m, 8H, aromatic) and 10.01 (s, 1H, NH). HRMS calcd 284.0715 (C$_{14}$H$_{15}$NO$_2$S.Na found 284.0716.

{[(4-fluorophenyl)sulfonyl]amino}-5-methylbenzoicacid (12). The title compound was synthesized by reacting 2-amino-5-methylbenzoic acid (0.25 g, 1.65 mmol), 4-fluoro-benzenesulfonyl chloride (0.39 g, 1.98 mmol) and sodium carbonate (0.36 g, 3.39 mmol) in 3 mL of water, following the reaction procedure of 10. The white solid obtained after acidification of reaction mixture was filtered, washed with water and dried to give 12 (0.44 g, 85.42%). Crystallization with EtOH gave (0.3 g) white amorphous solid, mp: 159-160° C.; IR (CHCl$_3$) 3177, 1662, 1342, 1148, 667 cm$^{-1}$; $^1$H NMR (500 MHz, CDCl$_3$) δ 2.31 (s, 3H, CH$_3$), 7.08-7.86 (m, 7H, aromatic), 9.32 (br, 1H, NH), and 10.18 (s, 1H, COOH). HRMS calcd 332.0363 (C$_{14}$H$_{12}$FNO$_4$S.Na$^+$), found 332.0372.

2-{[(4-fluorophenyl)sulfonyl]amino}-4-methylbenzenecarbonitrile (13). The title compound was synthesized by reacting 2-amino-4-methylbenzonitrile (0.25 g, 1.89 mmol) and 4-fluoro-benzenesulphonyl chloride (0.37 g, 1.89 mmol) in 2 mL of dry pyridine, following the reaction procedure of 6.$^{29}$ The concentrated reaction mixture was poured into ice cold water (300 mL), and resulting pale white solid was filtered, washed with water and dried to gave 13 (0.24 g, 42.8%). Crystallization with EtOH gave (0.15 g) white amorphous solid, mp: 130-132° C.; IR (CHCl$_3$) 3260, 2226, 1376, 1340, 1171, 1156 cm$^{-1}$; $^1$H NMR (500 MHz, CDCl$_3$) δ 2.42 (s, 3H, CH$_3$) and 6.90-7.83 (m, 7H, aromatic). HRMS calcd 313.0417 (C$_{14}$H$_{11}$FN$_2$O$_2$S.Na$^+$), found 313.0418.

(2-(1H-1,2,3,4-tetrazole-5-yl)-5-methylphenyl)[(4-fluorophenyl)sulfonyl]amine (14). The title compound was synthesized by reacting 2-{[(4-fluorophenyl)sulfonyl]amino}-4-methylbenzenecarbonitrile (13) (0.1 g, 0.34 mmol), sodium azide (0.09 g, 1.37 mmol), and ammonium chloride (0.74 g, 1.37 mmol) in 3 mL of DMF at 120° C. for 20 h.$^{23}$ Reaction mixture was poured into ice cold water (30 mL) and acidified with dilute HCl solution. The white precipitate obtained on acidification was extracted with ethyl acetate. The organic layer was washed (H$_2$O) dried (Na$_2$SO$_4$) and concentrated to give crude product (0.1 g), which was purified by FCC (silica gel, CH$_2$Cl$_2$, MeOH, CH$_3$COOH, 10:2:0.1, v/v/v) to give 13 as white solid (0.086 g, 74.9%) mp: 152-154° C.; IR (CHCl$_3$) 3136, 1457, 1376, 1348, 1165, 1153 cm$^{-1}$; $^1$H NMR (500 MHz, DMSOD$_6$) δ 2.36 (s, 3H, CH$_3$), 7.17-7.81 (m, 6H, aromatic) and 10.81 (br, 1H, NH). HRMS calcd 356.0587 (C$_{14}$H$_{12}$FN$_5$O$_2$S.Na$^+$), found 356.0587.

(4-methylphenyl)(phenylsulfonyl)amine (15). The title compound synthesized by triturating powdered mixture of p-toluedine (0.5 g, 4.66 mmol) and sodium bicarbonate (0.78 g, 9.33 mmol) with benzene sulfonyl chloride (0.82 g, 4.66 mmol) for 10 minutes at rt.$^{24A}$ Then reaction mixture was stirred with water, filtered, washed with water to remove sodium bicarbonate and dried to gave 15 (1.1 g, 95.14%). Product was purified by FCC using solvent gradient (silica gel, petroleum ether, ethyl acetate, triethyl amine, 9:1:0.2, v/v/v and petroleum ether and ethyl acetate 8:2, v/v) to give 15 as white needles (0.89 g), mp: 118-119° C. (lit$^{31B}$ 120-121° C.); IR (CHCl$_3$) 3254, 1510, 1389, 1330, 1163, cm$^{-1}$; $^1$H NMR (500 MHz, DMSOD$_6$) δ 2.27 (s, 3H, CH$_3$), 6.42 (br, 1H, NH), and 6.92-7.74 (m, 9H, aromatic). HRMS calcd 270.05592 (C$_{13}$H$_{13}$NO$_2$S.Na$^+$), found 270.05568.

[(4-Methylphenyl)sulfonyl]phenylamine (16). The title compound was synthesized by triturating aniline (0.5 g, 5.36 mmol), powdered sodium bicarbonate (0.9 g, 1.07 mmol) and powdered p-toluene sulfonyl chloride (1.02 g, 5.36 mmol) for 5 min at rt. The reaction mixture was stirred with water, filtered, washed with water and dried to give 16 (1.13 g, 84.9%). Product was purified by FCC by using eluent as in 15 to give 16 as white powder (0.9 g), mp-95-97° C. (lit$^{32A}$ 96° C.); IR(CHCl$_3$) 3255, 1599, 1342, 1160, cm$^{-1}$; $^1$H NMR (500 MHz, DMSOD$_6$) δ 2.37 (s, 3H, CH$_3$), 6.53 (br, 1H, NH), and 7.04-7.65 (m, 9H, aromatic). HRMS calcd 270.05592 (C$_{13}$H$_{13}$NO$_2$S.Na$^+$), found 270.05589.

Phenyl(phenylsulfonyl)amine (17). The title compound was synthesized by triturating aniline (0.5 g, 5.36 mmol), powdered sodium bicarbonate (0.9 g, 1.07 mmol) and benzene sulfonyl chloride (0.95 g, 5.36 mmol) for 10 min at rt. Then reaction mixture was stirred with water at 60° C. for 30 minutes, filtered, washed with water and dried to gave 17 (0.85 g, 68%). Product was purified by FCC by using eluent as in 15 to give 17 as white flakes (0.79 g), mp: 107-109° C. (lit$^{33A}$ 110° C.); IR (CHCl$_3$) 3256, 1599, 1331, 1162, cm$^{-1}$; $^1$H NMR (500 MHz, DMSOD$_6$) δ 6.4 (br, 1H, NH), and 7.04-7.77 (m, 10H, aromatic). HRMS calcd 256.04027 (C$_{12}$H$_{11}$NO$_2$S.Na$^+$), found 256.04016.

Methyl(4-methylphenyl)[(4-methylphenyl)sulfonyl] amine (18). The title compound was synthesized by adding methyl iodide (0.09 g, 0.63 mmol) to a stirring mixture of approximately 0.5 mL of 1-butyl-3-methyl-imidazolium-hexa-fluorophosphates, powdered KOH (0.04 g, 0.72 mmol) and 11 (0.15 g, 0.57 mmol) at rt.$^{25A}$ The reaction mixture stirred for 2 hours and then diluted with water, extracted with ethyl acetate. Organic layer was treated with brine solution, dried with Na$_2$SO$_4$ and evaporated to get thick liquid. Product was purified by FCC (silica gel, petroleum ether, ethyl acetate, 9:1, v/v) to give 18 as colorless viscous liquid, which solidified after several days (0.14 g, 88.5%), mp: 52-54° C. (lit$^{25A}$ 59-60° C.); IR (Neat) 1598, 1510, 1348, 1171, 1154, 679 cm$^{-1}$; $^1$H NMR (500 MHz, CDCl$_3$) δ 2.32 (s, 3H, CH$_3$), 2.41 (s, 3H, CH$_3$), 3.13 (s, 3H, CH$_3$), and 6.95-7.44 (m, 8H, aromatic). HRMS calcd 298.08722 (C$_{15}$H$_{17}$NO$_2$S.Na$^+$), found 298.08699.

(4-Methylphenyl)-N-(4-methylphenyl)carboxamide (19). The title compound was synthesized by adding (drop wise) solution of p-toluoyl chloride (0.86 g, 5.59 mmol) in 11 mL ethyl acetate (2 mL/mmol) to a solution of TEA (0.66 g, 6.5 mmol), p-toludine (0.5 g, 4.6 mmol) in 25 mL ethyl acetate (5 mL/mmol) at rt.[26A] The white precipitate obtained was stirred over-night. The next day, most of the solvent was removed in vacuo. Petroleum ether was added, and the solids were collected on a filter, washed twice with a mixture of petroleum ether/ethyl acetate (5/1) and three times with water. The residue was dried to obtain white crystalline needles (0.92 g, 85%). Crystallization from EtOH gave (0.75 g) white needle shaped shining crystals, mp: 163° C. (lit[34A] 163-164° C.); IR (nujol) 3202, 1669, 1341, 1167, 1149, cm$^{-1}$; $^1$H NMR (500 MHz, DMSO D$_6$) δ 2.16 (s, 3H, CH$_3$), 7.30-7.71 (m, 8H, aromatic) and 10.88 (br, 1H, COOH). HRMS calcd 248.10458 (C$_{15}$H$_{15}$NO.Na$^+$), found 248.10446.

(1E)-1-Aza-1,2-bis(4-methylphenyl)ethane (20). The title compound was synthesized by reacting p-toluedine (0.05 g, 0.46 mmol) and p-tolualdehyde (0.056 g, 0.46 mmol) for five minutes, then to this reaction mixture 3 mL of ethanol added and refluxed over-night.[27A] Next day solvent evaporated and crude product was purified by FCC (silica gel, petroleum ether, ethyl acetate, 9:1, v/v) to give 20 as yellow fluffy solid (0.045 g, 46%), mp: 83-85° C. (lit[35A] 107° C.); IR (CHCl$_3$) 3018, 2923, 2399, 1626, 1512, 1503, 1214, 751 cm$^{-1}$; $^1$H NMR (500 MHz, CDCl$_3$) δ 2.36 (s, 3H, CH$_3$), 2.41 (s, 3H, CH$_3$), 7.11-7.79 (m, 8H, aromatic) and 8.42 (s, 1H). HRMS calcd 232.10967 (C$_{15}$H$_{15}$N.Na$^+$), found 232.12772.

(4-Methylphenyl) [(4-methylphenyl)methyl]amine (21). Title compound was synthesized by reducing, the crude (1E)-1-aza-1,2-bis(4-methyl phenyl)ethane (20) in 4 mL methanol with sodium borohydride (0.15 g, 3.96 mmol) at rt for 10-20 min.[27] Methanol evaporated under vacuo and residue treated with saturated sodium bicarbonate solution and extracted with MDC. Organic layer dried with sodium sulfate and evaporated under vacuo to get crude 21. Crude product was purified by FCC (silica gel, petroleum ether, ethyl acetate, 9:1, v/v) to give 21 as pale yellow solid (0.079 g, 80%), mp: 50-51° C.; IR (CHCl$_3$) 3416, 3015, 2921, 2864, 1615, 1518, 1215, 810 cm$^{-1}$; $^1$H NMR (500 MHz, CDCl$_3$) δ 2.23 (s, 3H, CH$_3$), 2.33 (s, 3H, CH$_3$), 3.84 (br, 1H, NH), 4.25 (s, 2H), and 6.55-7.25 (m, 8H, aromatic). HRMS calcd 234.12532 (C$_{15}$H$_{17}$N.Na$^+$), found 234.12517.

(1E)-1-Aza-1-(4-methylphenyl)-2-phenylethene (22). The title compound was synthesized by reacting p-toluedine (0.2 g, 1.86 mmol) and benzaldehyde (0.198 g, 1.86 mmol) for five minutes, then to this reaction mixture 3 mL of ethanol added and refluxed for approx. 12 h.[27A] Next day solvent evaporated and crude product was purified by FCC (silica gel, petroleum ether, ethyl acetate, 9:1, v/v) to give 22 as colorless liquid (0.155 g, 42%), IR (CHCl$_3$) 3023, 1626, 1512, 1504, 1190, 814, 691 cm$^{-1}$; $^1$H NMR (500 MHz, CDCl$_3$) δ 2.36 (s, 3H, CH$_3$), 7.13-7.89 (m, 9H, aromatic) and 8.46 (s, 1H). HRMS calcd 218.09402 (C$_{14}$H$_{13}$N.Na$^+$), found 218.09387.

(4-Methylphenyl)benzylamine (23). The title compound was synthesized by reducing, the crude (1E)-1-aza-1-(4-methylphenyl)-2-phenylethene (22) in 6 mL methanol with sodium borohydride (0.6 g, 15.8 mmol) at rt for 10-20 minutes.[27A] Methanol evaporated under vacuo and residue treated with saturated sodium bicarbonate solution and extracted with MDC. Organic layer dried with sodium sulfate and evaporated under vacuo to get crude 23. Crude product was purified by FCC (silica gel, petroleum ether, ethyl acetate, 9:1, v/v) to give 23 as colorless low melting solid (0.32 g, 86%), mp 20° C.; IR (CHCl$_3$) 3414, 3025, 2357, 1616, 1520, 806 cm$^{-1}$; $^1$H NMR (500 MHz, CDCl$_3$) δ 2.22 (s, 3H, CH$_3$), 3.88 (s, 1H, NH), 4.29 (s, 2H), and 6.54-7.36 (m, 9H, aromatic). HRMS calcd 220.10967 (C$_{14}$H$_{15}$N.Na$^+$), found 220.10936.

Combination Therapies

In addition to a single therapy, which is the case with the administration of, for example, a single compound of the invention, cancer treatments are commonly combined with other methods of treating cancer. Combination therapy includes combining the method of treating cancer as described in the invention and one or more cancer therapeutic methods. Cancer therapeutic methods include surgical therapy, radiation therapy, administering an anticancer agent (including, for example, antineoplastics (including, for example, novantrone, bicalutamide, esterified estrogens, goserelin, histrelin, leuprolide, nilandron, triptorelin pamoate, docetaxel, taxotere, carboplatin, and cisplatin) or combinations thereof, and angiogenesis inhibitors), immunotherapy, antineoplastons, investigational drugs, vaccines, less conventional therapies (sometimes referred to as novel or innovative therapies, which include, for example, chemoembolization, hormone therapy, local hyperthermia, photodynamic therapy, radiofrequency ablation, stem cell transplantation, and gene therapy), prophylactic therapy (including, for example, prophylactic mastectomy or prostatectomy), and alternative and complementary therapies (including, for example, dietary supplements, megadose vitamins, herbal preparations, special teas, physical therapy, acupuncture, massage therapy, magnet therapy, spiritual healing, meditation, pain management therapy, and naturopathic therapy (including, for example, botanical medicine, homeopathy, Chinese medicine, and hydrotherapy)).

It is to be understood that the functional capabilities of the embodiments of the current invention are exemplary and not intended to be limiting. The biological activity that may be encompassed by the embodiments of the current invention may be directly identified or inherently expressed by the chemical compound structures shown. The methods include various steps that may be taken in the presented order or be alternatively sequenced in various manners as may be contemplated by those of ordinary skill in the art. It is further contemplated that additional functional capabilities inherent to the structural embodiments of the current invention may be utilized within the methods of the current invention. Further, any specific order or hierarchy of functional capabilities described herein are merely exemplary approaches and based upon design preferences may be rearranged while remaining with the scope and spirit of the present invention. The methods may employ the above described functional capabilities in various ways, enabling one or many of the features without regard to any specific hierarchical order.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof.

All references cited herein are specifically incorporated by reference.

REFERENCES

1. *Cancer Statistics* 2005; American Cancer society: Washington, D.C., 2006.
1A. Jemal, A.; Siegel, R.; Ward, E.; Murray, T.; Xu, J. Q.; Thun, M. J. Cancer statistics, 2007. CA Cancer J. Clin. 2007, 57(1), 43-66.
2. Isaacs, J. T.; Coffey, D. S. Adaptation versus selection as the mechanism responsible for the relapse of prostatic cancer to androgen ablation therapy as studied in the Dunning R-3327-H adenocarcinoma. *Cancer Res.*, 1981, 41, 4070-5075.
2A Ross, R. K.; Pike, M. C.; Coetzee, G. A.; Reichardt, J. K.; Yu, M. C.; Feigelson, H.; Stanczyk, F. Z.; Kolonel, L. N.; Henderson, B. E. *Cancer Res.* 1998, 58(20), 4497-4504.
3. Bruchovsky, N.; Rennie, P. S.; Coldman, A. J.; Goldenberg, S. L.; To, M.; Lawson, D. Effects of androgen withdrawal on the stem cell composition of the Shionogi carcinoma. *Cancer Res.*, 1990, 50, 2275-2282.
3A. Goldenberg, S. L.; Bruchovsky, N. *Urol. Clin. North. Am.* 1991, 18(1), 111-122.
4. Ferrari, A. C.; Chachoua, A.; Singh, H.; Rosenthal, M.; Taneja, S.; Bendnar, M.; Mandeli, J.; Muggia, F. A Phase I/II study of weekly paclitaxel and 3 days of high dose oral estramustine in patients with hormone-refractory prostate carcinoma. *Cancer,* 2001, 91, 2039-2045.
4A. de Voogt, H. J. Prostate 1992, (Suppl. 4), 91-95.
5. Taplin, M-E.; Balk, S. P. Androgen receptor: A key molecule in the progression of prostate cancer to hormone independence. *J. Cellular Biochem.* 2004, 91, 483-490.
5A de Voogt, H. J.; Smith, P. H.; Pavone-Macaluso, M.; de Pauw, M.; Suciu, S. *J. Urol.* 1986, 135, (2), 303-307.
6. Santos, A. F.; Huang, H.; Tindall, D. J. The androgen receptor: a potential target for the therapy of prostate cancer. *Steroids,* 2004, 69, 79-85.
6A. Kelly, W. K.; Scher, H. I. *J. Urol.* 1993, 149(3), 607-609.
7. Chen, C. D.; Welsbie, D. S.; Tran, C.; Baek, S. H.; Chen, R.; Vessella, R.; Rosenfeld, G. M.; Sawyer, C. L. Molecular determinants of resistance to antiandrogen therapy. *Nat. Med.*, 2004, 10, 33-39.
7A. Suzuki, H.; Akakura, K.; Komiya, A.; Aida, S.; Akimoto, S.; Shimazaki, *J. Prostate* 1996, 29(3), 153-158.
8. Suzuki, H.; Ueda, T.; Ichikawa, T.; Ito, H. Androgen receptor involvement in the progression of prostate cancer. *Endo. Realt. Cancer,* 2003, 10, 209-216.
8A. Bohl, C. E.; Gao, W.; Miller, D. D.; Bell, C. E.; Dalton, J. T. *Proc. Natl. Acad. Sci. U.S.A.* 2005, 102(17), 6201-6206.
9. Mohler, J. L.; Gregory, C. W.; Harris Ford III, O.; Kim, D.; Weaver, C. M.; Petrusz, P.; Wilson, E. M.; French, F. S. The androgen axis in recurrent prostate cancer. *Clin. Cancer Res.*, 2004, 10, 440-448.
10. Handratta, V. D.; Vasaitia, T. S.; Njar, V. C. O.; Gediya, L. K., Kataria, R.; Chopra, P.; Newman, Jr., D.; Farquhar, R.; Guo, Z.; Qiu, Y.; Brodie, A. M. H. Novel C-17-heteroaryl CYP17 inhibitors/antiandrogens: Synthesis, in vitro biological activity, pharmacokinetics, and antitumor activity in the LAPC4 human prostate cancer xenograft model. *J. Med. Chem.*, 2005, 48, 2972-2984.
11. Ren, F.; Zhang, S.; Mitchell, S. H.; Butler, R.; Young, C. Y. F. Tea polyphenols down-regulate the expression of the androgen receptor in LNCaP prostate cancer cells. *Oncogene,* 2000, 19, 1924-1932.
12. Xing, N.; Chen, Y.; Mitchell, S. H.; Young, C. Y. F. Quercetin inhibits the expression and function of the androgen receptor in LNCaP prostate cancer cells. *Carcinogenesis,* 2001, 22, 409-414.
13. Zhang, Y.; Ni, J.; Messing, E. M.; Chang, E.; Yang, C-R.; Yeh, S. Vitamin E succinate inhibits the function of androgen receptor and the expression of prostate-specific antigen in prostate cancer cells. *Proc. Natl. Acad. Sci. USA,* 2002, 99, 7408-7413.
14. Nakamura, K.; Yasunaga, Y.; Segawa, T.; Ko, D.; Moul, J. W.; Srivastava, S.; Rhim, J. S. Curcumin down-regulates AR gene expression and activation in prostate cancer cell lines. *Int. J. Oncol.,* 2002, 21, 852-830.
15. Thompson, T. A.; Wilding, G. Androgen antagonist activity by the antioxidant moiety of vitamin E, 2,2,5,7,8,-pentamethyl-6-chromanol in human prostate carcinoma cells. *Mol. Caner. Ther.,* 2003, 2, 797-803.
16. Young, C. Y.; Jatoi, A.; Ward, J. F.; Blute, M. L. The effects of dietary factors on the androgen receptor and related cellular factors in prostate cancer. *Curr. Med. Chem.,* 2004, 7, 909-923.
17. Zhu, W.; Smith, A.; Young, C. Y. F. A nonsteroidal anti-inflammatory drug, flufenamic acid, inhibits the expression of the androgen receptor in LNCaP cells. *Endocrinology,* 1999, 140, 5451-5454.
18. Chen, L.; Meng, S.; Wang, H.; Bali, P.; Bai, W.; Li, B.; Atadja, P.; Bhalla, K. N.; Wu, J. Chemical ablation of androgen receptor in prostate cancer cells by the histone deacetylase inhibitor LAQ824. *Mol. Cancer. Ther.,* 2005, 4, 1311-1319.
19. Bonham, M.; Posakony, J.; Coleman, I.; Montgomery, B.; Simon, J.; Nelson, P. S. Characterization of chemical constituents in *Scutellaria baicalensis* with antiandrogenic and growth-inhibitory activities toward prostate carcinoma. Clin. *Cancer Res.,* 2005, 11, 3905-3914.
20. Ohtsu, H.; Itakawa, H.; Xiao, Z.; Su, C.-Y.; Shih, C. C. Y.; Chiang, T.; Chang, E.; Lee, Y.; Chiu, S.-Y.; Chang, C.; Lee, K.-H. Antitumor agents 222. Synthesis and anti-androgen activity of new diarylheptanoids. *Bioorg. Med. Chem.,* 2003, 11, 5083-5090.
21. Ohtsu, H.; Xiao, Z.; Ishida, J.; Naggai, M.; aWang, H.-K.; Itakawa, H.; Su, C.-Y.; Shih, C.; Chiang, T.; Chang, E.; Lee, Y.; Tsai, M.-Y.; Chang, C.; Lee, K.-H. Antitumor agents. 217. Curcumin analogues as novel androgen receptor antagonist with potential as anti-prostate cancer agents. *J. Med. Chem.,* 2002, 45, 5037-5042.
22. Lin, L.; Shi, Q.; Su, C.-Y.; Shih, C. C. Y.; Lee, K.-H. Antitumor agents 247. New 4-thoxycarbonylethyl curcumin analogs as potential antiandrogenic agents. *Bioorg. Med. Chem.,* 2006, 14, 2527-2534.
23. Lin, L.; Shi, Q.; Nyarko, A. K.; Bastow, K. F.; Wu, C.-C.; Su, C.-Y.; Shih, C. C.-Y.; Lee, K-H. Atitumor agents. 250. Design and synthesis of new curcumin analogs as potential anti-prostate cancer agents. *J. Med. Chem.;* 2006, 49, 3963-3972.
23A. Gallardo, H.; Begnini, I. M.; Neves, A.; Vencato, I. *J. Braz. Chem. Soc.* 2000, 11, 274-280.
24. Guner, O. F. Pharmacophore perception, development, and use in drug design. International University Line: La Jolla, Calif., 2000.
24A. Massah, A. R.; Kazemi, F.; Azadi, D.; Farzaneh, S.; Aliyan, H.; Naghash, H. J.; Momeni, A. R. *Lett. Org. Chem.* 2006, 3(3), 235-241.
25. Dror, O.; Shulman-Peleg, A.; Nussinov, R.; Wolfson, H. L. Predicting molecular interactions in silico: 1. A guide to pharmacophore identification and its application to drug design. *Curr. Med. Chem.,* 2004, 11, 71-90.
25A. Hu, Y.; Chen, Z. C.; Le, Z. G.; Zheng, Q. G. *Org. Prep. Proced. Int.* 2004, 36(4), 347-351.
26. Lyne, P. D.; Kenny, P. W.; Cosgrove, D. A.; Deng, C.; Zabludoff, S.; Wendoloski, J. J.; Ashwell, S. Identification of compounds with nanomolar binding affinity for checkpoint kinase-1 using knowledge-based virtual screening. *J. Med. Chem.*, 2004, 47, 1962-1968.

26A. van den Nieuwendijk, A. M.; Pietra, D.; Heitman, L.; Goblyos, A.; A P, I. *J. Med. Chem.* 2004, 47(3), 663-672.

27. Clement, O. O.; Freeman, C. M.; Hartmann, R. W.; Handratta, V. D.; Vasaitis, T. S.; Brodie, A. M. H.; Njar, V. C. O. Three dimensional pharmacophore modeling of human CYP17 inhibitors. Potential agents for prostate cancer therapy. *J. Med. Chem.;* 2003, 46, 2345-2351.

27A. Kovat, E. M.; Langer, T. *J. Med. Chem.* 2003, 46, 716-726.

28. 27B. Palma, A.; Barajas, J. J.; Kouznetsov, V. V.; Stashenko, E.; Bahsas, A.; Amaro-Luis, J. *Synlett.* 2004, 15, 2721-2724. Njar, V. C. O.; Purushottamachar, P.; Khandelwal, A.; Maheshwari, N.; Chopra, P.; Gediya L. K. First Three-dimensional Phramacophore Modeling of Androgen Receptor Down-regulating Agents (ARDAs): Discovery of Potent Anti-Prostate Cancer Agents. 232$^{nd}$ *American Chemical society (ACS) National Meeting, San Francisco, Calif., USA, Sep.* 10-14, 2006, Abstract #: MEDI 75.

29. Huppatz J. L.; Sasse W. H. F. Pschorr reactions with sulphonamides derived from N-benzyle-o-phenylenediamine: A new route of phenanthridine and new type of molecular rearrangement. *Aust. J. Chem.,* 1963, 16, 417-431.

29A Njar, V. C. O.; Purushottamachar, P.; Khandelwal, A.; Maheshwari, N.; Chopra, P.; Gediya L. K. 232nd American Chemical society (ACS) National Meeting, San Francisco, Calif., USA, Sep. 10-14, 2006, Abstract #MEDI 75.

30. Scheifele, H. J.; DeTar, D. F. 2-Aminobenzophenone. *Org. Syn. Coll. Vol. IV,* 1963, 34-38.

30A Bahattacharjee, A. K.; Dheranetra, W.; Nichols, D. A.; Gupta, R. K. QSAR Comb. Sci. 2005, 24, 593-602.

31. Fanta, P. E.; Wang. C. Derivatives of 2-(nitromethyl) quinoline. *J. Het. Chem.* 1996, 3, 525-526.

31A. Delfin, D. A.; Bahattacharjee, A. K.; Yakovich, A. J.; A Werbovetz, K. A. *J. Med. Chem.* 2006, 49, 4196-4207.

31B. Badr, M. Z. A.; Aly, M. M.; Fahmy, A. M. *J. Org. Chem.* 1981, 46(23), 4784-4787.

32. Fadda A. A.; Khalil A. M.; El-Habbal, M. M. Syntheis of certain sulphonamides and amino pyranoquinoline derivatives from 4-hydroxyquinoline with biological interest. *Pharmazie,* 1991, 46, 743-44.

32A. Gowda, B. T.; Jayalakshmi, K. L.; Shetty, M. *Zeitschrift Fur Naturforschung Section A Journal of Physical Sciences* 2004, 59(4-5), 239-249.

33. Yashuhara A.; kameda M.; Sakamoto T. Selective monodesulfonylation of N,N-disulfonylamines with tetrabutyl ammonium floride. *Chem. Pharm. Bul.* 1999, 47, 809-812.

33A. Hellwinkel, D.; Supp, M. *Chem. Ber.* 1976, 109(12), 3749-3766.

34. Yokoi, A.; Kuromitsu, J.; Kawal, T.; Nagasu, T.; Sugi, N. H.; Yoshimatsu, K.; Yoshino, H.; Owa, T. Profiling novel sulfonamide antitumor agents with cell-based phenotypic screens and array-based gene expression analysis. *Molec. Caner Thera.,* 2002, 1, 275-286.

34A. Ito, S.; Tanaka, Y.; Kakehi, A. *Bull. Chem. Soc. Jpn* 1982, 55(3), 859-864

35. Kawai, M.; BaMaung, N. Y.; Fidanze, S. D.; Erickson, S. A.; Tedrow, J. S.; Sanders, W. J.; Vasudevan, A.; Park, C.; Hutchins, C.; Comess, K. M.; Kalvin, D.; Wang, J.; Zhang, Q.; Lou, P.; Tucker-Garcia, L.; Bouska, J.; Bell, L. R.; Lesniewski, R.; Henkin, J.; Shappard, G. S. Development of sulfonamide compounds as potent methionine aminopeptidase type II inhibitors with antiproliferative properties. *Bioorg. Med. Chem. Lett.,* 2006, 16, 3574-3577.

35A. Manrao, M. R.; Khera, V.; Sharma, J. R. *Journal of Research (Punjab Agricultural University)* 2005, 42(1), 48-52.

36. Hu, L.; Li, Z-R.; Li, Y.; Qu, J.; Ling, Y-H.; Jiang, J-D.; Boykin, D. W. Synthesis and structure-activity relationships of carbazole sulfonamides as novel class of antimitotic agents against solid tumors. *J. Med. Chem.,* 2006, 49, 6273-6282.

37. Allison, B. D.; Phuong, V. K.; McAtee, L. C.; Rosen, M.; Morton, M.; Prendergast, C.; Barrett, T.; Lagaud, G.; Freedman, J.; Li, L.; Wu, X.; Venkatesan, H.; Pippel, M.; Woods, C.; Rizzolio, M. C.; Hack, M.; Hoey, K.; Deng, X.; King, C.; Shankley, N. P.; Rabinowitz, M. H. Identification and optimization of antranilic sulfonamides as novel, selective cholecystokinin-2 receptor antagonists. *J. Med. Chem.,* 2006, 49, 6371-6390.

38. *Catalyst*, release version 4.10; Accelrys, 9685 Scranton Road, San Diego, Calif. 92121.

39. Brooks, B. R.; Bruccoleri, R. E.; Olafson, B. D.; States, D. J.; Swaminathan, S.; Karplus, M. CHARM: A program for macromolecular energy, minimization and dynamics calculations. *J. Comput. Chem.* 1983, 4, 187-217.

40. Smellie, A.; Teig, S. L.; Towbin, P. Poling: promoting conformational variation. *J Comput. Chem.* 1995, 16, 171-187.

41. Sprague, P. W. Automated Chemical Hypothesis Generation and Database Searching with Catalyst. In *Perspectives in Drug Discovery and Design*; Müller, K., Ed.; ESCOM Science Publishers B. V.: Leiden, The Netherlands, 1995; Vol. 3, pp 1-20.

42. Greene, J.; Kahn, S.; Savoj, H.; Sprague, P.; Teig, S. Chemical Function Queries for 3D Database Search, *J. Chem. Inf. Comput. Sci.* 1994, 34, 1297-1308.

43. Clement, O. O.; Trope-Mehl, A. HipHop: Pharmacophores based on multiple common-feature alignments. In *Pharmacophore Perception, Development, and Use in Drug Design*; Güner, O. F., Ed.; International University Line: La Jolla, Calif., 2000; pp 69-83.

What is claimed is:

1. A method for inhibiting androgen activity in a subject in need thereof comprising administering to said subject a therapeutically effective amount of a pharmaceutical composition comprising
an androgen inhibition activity compound of structure (1); and
a pharmaceutically acceptable carrier, diluent or excipient,

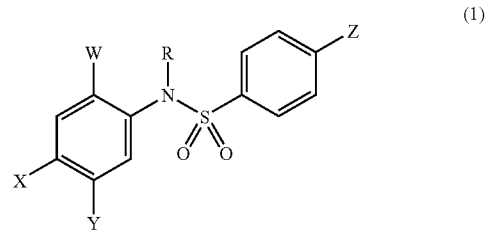

wherein
W is selected from the group consisting of H, cyano, —NO$_2$, —COOH and a heterocyclic group;
X is selected from H, unsubstituted linear or branched alkyl group and halogen,
Y is selected from H and substituted or unsubstituted linear and branched alkyl group, Z is selected from H, substituted or unsubstituted linear and branched alkyl group,
and
R is selected from H and substituted or unsubstituted linear and branched alkyl group.

2. A method for inhibiting androgen activity in a subject in need thereof comprising administering to said subject a therapeutically effective amount of a pharmaceutical composition comprising an androgen inhibition activity compound is selected from the group consisting of [(4-Methylphenyl)sulfonyl](2-nitrophenyl)amine, (2-Nitrophenyl)(phenylsulfonyl)amine, (4-Methyl-2-nitrophenyl)(phenylsulfonyl)amine, [(4-Fluorophenyl)sulfonyl](4-methyl-2-nitrophenyl)amine, 5-Methyl-2-[(phenylsulfonyl)amino]benzoic acid, and [(4-Methylphenyl)[(4-methylphenyl)sulfonyl]amine.

3. The method of claim 1, wherein
W is selected from the group consisting of H, cyano, —NO$_2$, —COOH and 1H-tetrazole;
X is selected from H, methyl and F,
Y is selected from H, methyl and F,
Z is selected from H and methyl,
and
R is selected from H and methyl.

4. The method of claim 1, wherein said androgen inhibition activity compound is a compound of formula BTB01434 or 6-18:

| Compound | W | X | Y | Z |
|---|---|---|---|---|
| BTB01434 | NO$_2$ | CH$_3$ | H | CH$_3$ |
| 6 | NO$_2$ | H | H | CH$_3$ |
| 8 | NO$_2$ | CH$_3$ | H | H |
| 7 | NO$_2$ | H | H | H |
| 9 | NO$_2$ | CH$_3$ | H | F |
| 11 | H | CH$_3$ | H | CH$_3$ |
| 10 | COOH | CH$_3$ | H | H |
| 12 | COOH | CH$_3$ | H | F |
| 13 | CN | H | CH$_3$ | F |
| 14 | 1H-tetrazole | H | CH$_3$ | F |
| 15 | H | CH$_3$ | H | H |
| 16 | H | H | H | CH$_3$ |
| 17 | H | H | H | H |
| 18 | H | CH$_3$ | CH$_3$ | CH$_3$. |

5. The method of claim 1, wherein said androgen inhibition activity comprises activity selected from the group consisting of decreasing androgen synthesis or concentration, AR down-regulation and/or AR modulation, and preventing the binding of an androgen to an androgen receptor or competing with an androgen and its binding to an androgen receptor.

6. The method of claim 1, wherein said androgen inhibition activity compound comprises a marker.

7. The method of claim 6, wherein said marker allows identification when the compound is bound with a cancer cell.

* * * * *

UNITED STATES PATENT AND TRADEMARK OFFICE
CERTIFICATE OF CORRECTION

PATENT NO. : 7,960,435 B2
APPLICATION NO. : 12/519233
DATED : June 14, 2011
INVENTOR(S) : Vincent C. O. Njar et al.

Page 1 of 1

It is certified that error appears in the above-identified patent and that said Letters Patent is hereby corrected as shown below:

On the Title Page

<u>Item (75)</u>:
Change the second inventor's name from:
"Puranik Purushottamachar, Philadelphia, PA (US)"
To be:
-- Purushottamachar Puranik, Gaithersburg, MD (US) --

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*